United States Patent
Totsuka et al.

(10) Patent No.: US 7,364,874 B2
(45) Date of Patent: Apr. 29, 2008

(54) MEDIUCM FOR DETECTING VAN A AND VAN B VANCOMYCIN-RESISTANT ENTERCOCCI AND METHOD OF USING THE SAME

(75) Inventors: Kyoichi Totsuka, Tokyo (JP); Ken Kikuchi, Tokyo (JP); Yutaka Uzawa, Souka (JP)

(73) Assignee: Tokyo Women's Medical University, Tokyo (JP)

( * ) Notice: Subject to any disclaimer, the term of this patent is extended or adjusted under 35 U.S.C. 154(b) by 510 days.

(21) Appl. No.: 10/488,309

(22) PCT Filed: May 17, 2002

(86) PCT No.: PCT/JP02/04766

§ 371 (c)(1),
(2), (4) Date: Mar. 3, 2004

(87) PCT Pub. No.: WO03/020918

PCT Pub. Date: Mar. 13, 2003

(65) Prior Publication Data

US 2004/0241747 A1    Dec. 2, 2004

(30) Foreign Application Priority Data

Sep. 3, 2001    (JP) .............................. 2001-265463

(51) Int. Cl.
- C12Q 1/18    (2006.01)
- C12Q 1/20    (2006.01)
- C12Q 1/04    (2006.01)
- C12Q 1/16    (2006.01)

(52) U.S. Cl. ............................. 435/32; 435/33; 435/34; 435/35

(58) Field of Classification Search ............ 435/32–35
See application file for complete search history.

(56) References Cited

FOREIGN PATENT DOCUMENTS

JP    7-303477    11/1995

OTHER PUBLICATIONS

Eisgruber. (1995) Int. vol. 28 No. 3 p. 219-226.*
Lee et al. 2001, Letters in Applied Microbiology, vol. 33 pp. 349-351.*
McDowell et al. Microbios (1989) 57:187-204.*
Arthur et al. Antimicrobial Agents Chemotherapy. (1992) vol. 36 No. 4 p. 867-869.*
Green et al. 1981, Journal of Clinical Microbiology, vol. 28 No. 3 pp. 484-488.*
Wise et al. Antimicrobial Agents Chemotherapy (1984) vol. 25 No. 5 p. 612-613-617.*
Arthur et al. Aug. 1999 Antimicrobial Agents and Chemotherapy vol. 43 p. 1875-1880.*
R. Hartemink et al., LAMVAB-A new selective medium for the isolation of lactobacilli from faeces., Journal of Microbiological Methods (1997), vol. 29, No. 2, pp. 77 to 84.

* cited by examiner

*Primary Examiner*—Mark Navarro
(74) *Attorney, Agent, or Firm*—Young & Thompson

(57) ABSTRACT

Van A and Van B vancomycin resistant *enterococci* detection media as well as a method of selectively detecting Van A and Van B vancomycin resistant *enterococci* clinically important in vancomycin resistant *enterococci* from testing microorganisms or specimens using the media. The media for selectively detecting Van A and Van B VRE from testing microorganisms and specimens are media where *enterococci* can grow where vancomycin, D-cycloserine and D-lactate are added. Preferably 32-256 μg/ml of vancomycin, 1-64 μg/ml of D-cycloserine, and 0.025-0.8 mol/l of sodium lactate are added to culture medium where *enterococci* can grow.

8 Claims, No Drawings

MEDIUCM FOR DETECTING VAN A AND VAN B VANCOMYCIN-RESISTANT ENTERCOCCI AND METHOD OF USING THE SAME

TECHNICAL FIELD OF THE INVENTION

The present invention relates to a medium for detecting Van A and Van B vancomycin resistant *enterococci* and a method of detecting Van A and Van B vancomycin resistant *enterococci* by using the medium. Particularly, the invention relates to a medium with certain formula for detecting Van A and Van B vancomycin resistant *enterococci* and to a method of selectively detecting clinically important Van A and Van B vancomycin resistant *enterococci* in test microorganisms or specimens by using said medium.

PRIOR ART

*Enterococci*, as its name implies, are catalase negative and Gram positive cocci, forming indigenous microbial flora in the intestine and including about 20 organisms. Conventionally, *enterococci* had been classified as a part of *Streptococcus* species but have been classified as an independent species, *enterococci*, because of DNA homology and 16S ribosomal RNA sequence analysis, etc. Clinically, *enterococci* are primarily found in the urinary tract and the biliary tract, and are often causative agents for sepsis and infectious endocarditis. *Enterococcus faecalis* is the most frequently isolated organism, followed by *Enterococcus faecium* and *Entorococcus avium*. Other enterococal species are rarely isolated. *Enterococcus faecalis* is a main species which is known to have pathogenic factors such as hemolytic toxin and protease, but basically enterococcal species are thought to be weakly pathogenic.

*Enterococci* are naturally resistant to cephem antibiotics and many of them are resistant to aminoglycoside, macrolide, tetracycline, chloramphenicol, penicillin, lincomycin antibiotics, etc. Since 1980's when the third generation cephem antibiotics were introduced, the nosocomial infection caused by multi-resistant *enterococci* has been reported. Because *enterococci* are indigenous microorganisms in the intestine, in most cases, feces are the source of the nosocomial infection. It is pointed out that hands of health care workers and hospital environment are involved in the infection. If drug resistant *enterococci* emerge, they are expected to quickly spread to communities because *enterococci* are also indigenous in the intestine of many of domestic and pet animals and are detected from sewages and their processing facilities.

Vancomycin resistant *enterococci* (hereinafter referred to as VRE) were reported in the late 1980's in Europe and has quickly spread from the US and Europe to all over the world. People pay great attention to VRE as the most difficult nosocomial infection organism in treatment. VRE are *enterococci* that have rendered themselves resistant to vancomycin and, as a result, show resistance to almost all existing antibiotics. There are no antibiotics which ensure clinical effectiveness against VRE infection except for those currently being developed. There are some isolated deaths from serious infection such as sepsis. Vancomycin resistant genes are known to be transferred to various Gram positive microorganisms through plasmids or chromosomes. People are concerned about the risk of transferring of vancomycin resistant genes to methicillin resistant *Staphylecoccus aureus* (hereinafter referred to as MRSA) to which vancomycin is the only effective drug.

CDC (Centers for Disease Control and Prevention) reported recent increase in the clinical VRE isolation rate and presented detailed measures, stating that each medical institution should establish its own comprehensive strategy which suits to each facility in order to check, prevent and control VRE infection and settlement. In the report; CDC says that microorganism testing laboratories are front lines preventing VRE transmission in the hospitals and are required to have the ability to identify *enterococci* quickly and precisely and to detect VRE in order to find VRE infection and settlement. This is to save labor-intensive containment which is complex and costly and which will become necessary when the detection of VRE infection is delayed. CDC also suggested detailed VRE detection tests and emphasized the importance of the detection tests.

VRE has been also frequently reported in Japanese medical institutions recently and has been reported to be detected in meats etc. Thus people are concerned about the spread of VRE in Japan. "Infectious disease control laws" were considerably revised in April, 2000, and "laws for infection prevention and treatment for patients with infectious disease" were put into effect. In the laws, VRE infection is designated as Class IV infection, meaning that all the infections have to be reported. Currently, VRE is categorized in six types, Van A VRE, Van B VRE, Van C VRE, Van D VRE, Van E VRE and Van G VRE, depending on resistance genes. These VREs show different resistance patterns against vancomycin and teicoplanin which is a glycopeptide antibiotic and a vancomycin homologue, depending on their resistance genes. The resistance patterns are shown below:

Van A VRE carries van A gene as a resistance gene, and the minimum inhibitory concentration (hereinafter referred to as MIC) of vancomycin is 64->1000 µg/ml and the MIC of teicoplanin is 16-512 µg/ml.

Van B VRE carries van B gene as a resistance gene, and the MIC of vancomycin is 4->1000 µg/ml and the MIC of teicoplanin is 0.5-1 µg/ml.

Van C VRE carries van C gene as a resistance gene, and the MIC of vancomycin is 2-32 µg/ml and the MIC, of teicoplanin is 0.5-1 µg/ml.

Van D VRE carries van D gene as a resistance gene, and the MIC of vancomycin is 64-1024 µg/ml and the MIC of teicoplanin is 4-1024 µg/ml.

Van E VRE carries van E gene as a resistance gene, and the MIC of vancomycin is 16 µg/ml and the MIC of teicoplanin is 0.5 µg/ml.

Van G VRE carries van G gene as a resistance gene, and the MIC of vancomycin is 12-16 µg/ml and the MIC of teicoplanin is 0.5 µg/ml.

Of the above VREs, Van A VRE and Van B VRE are clinically significant because the resistance genes thereof can be transmitted to other Gram positive strains through plasmids and chromosomes, and are resistant to many current antibiotics. In the whole description of the invention in the specification and claims, "Van A and Van B VRE" means "Van A VRE" and "Van B VRE." In contrast, Van C VRE is clinically less significant because Van C gene is a natural resistance gene which *Enterococcus casseliflavus, Enterococcus gallinarum, Enterococcus flavescens*, etc originally have, is not transmissible and has relatively low resistance to various antibiotics.

Van D VRE, Van E VRE and Van G VRE are clinically less significant because they have been reported only several times in the whole world and are not transmissible.

As described above, Van A and Van B VRE are clinically very significant because there are no effective treatments for infection thereof, and they have risks of causing contamination widely in in- and out-hospital environments and of causing serious nosocomial infection. Hence it is recommended that medical institutions carry out screening tests for VRE to detect Van A and Van B VRE. The screening tests should be quick and precise, too. Currently, the following VRE screening tests are carried out:

*Enterococci* constitute a part of the indigenous bacterial flora of the intestine so that the intestine draws attention as a site carrying VRE. Thus for VRE screening tests, fecal specimens and rectal swabs are mainly used. In the case these specimens are used for VRE screening tests, they are directly inoculated to *enterococci* selective media containing 6-8 µg/ml of vancomycin, and incubated at 35-37° C. for 24 to 48 hours. Colonies grown on the media are tested for identification, vancomycin susceptibility and detection of resistance genes to detect VRE. The *enterococci* selective media containing 6-8 µg/ml of vancomycin used here are commercially available from several medium manufacturers as the VRE selective medium.

However, VRE selective media currently used for testing allow growth of clinically less significant Van C VRE as well as clinically significant Van A and Van B VRE.

In addition, it is impossible to differentiate on the media between Van A and Van B VRE, and Van C VRE which grow on the media.

When VRE screening tests are carried out using VRE selective media currently used for testing, additional tests should be carried out to determine whether grown VRE is clinically significant Van A and Van B VRE or clinically less significant Van C VRE.

Van C VRE is indigenous in the intestine of healthy individuals. Thus if VRE screening tests are carried out using VRE selective media currently available and specimens such as feces and the like, numerous Van C VRE would be detected. Accordingly current testing methods becomes complex because said additional tests are required.

In addition, it is highly likely that Van A and Van B VRE could be missed when both of clinically significant Van A and Van B VRE and clinically less significant Van C VRE are present in specimens.

Furthermore, some Van B VRE with a low vancomycin MIC grow very poorly on currently used VRE selective media. Said strains sometimes do not grow on said media at all so that if this kind of strains exists in specimens, it is highly likely that the strains are not detected.

Altogether, if selective media used for VRE screening suppress the growth of Van C VRE but support the growth of Van A and Van B VRE alone, they can reduce escapees in detection and improve by leaps and bounds the complex procedures accompanied with current tests.

SUMMARY OF THE INVENTION

The present inventors took the above into account and intended to develop Van A and Van B VRE detection media that allow the selective growth of clinically significant Van A and Van B VRE but suppress the growth of clinically less significant Van C VRE. We focused on and studied the vancomycin resistant mechanism of Van A and Van B VRE and found substances supporting the cell wall synthesis system of Van A and Van B VRE. We successfully made detection media that selectively grow clinically significant Van A and Van B VRE but suppress the growth of clinically less significant Van C VRE by adding the substances to media and completed this invention.

The invention provides Van A and Van B VRE detection media that selectively grow clinically significant Van A and Van B VRE as well as a method of selectively detecting Van A and Van B VRE from testing microorganisms and specimens using said media so that detection miss is reduced and complex testing procedures currently used are improved.

To solve the above problems, the invention described in claim 1 is a Van A and Van B VRE detection medium where vancomycin, D-cycloserine and D-lactate are added to a culture medium formula where *enterococci* can grow.

The invention described in claim 2 is a Van A and Van B VRE detection medium where 32-256 µg/ml of vancomycin, 1-64 µg/ml of D-cycloserine and 0.025-0.8 mol/L of DL-sodium lactate are added to a culture medium formula where *enterococci* can grow. The invention described in claim 3 is a method of selectively detecting Van A and Van B VRE from testing microorganisms and specimens using a Van A and Van B VRE detection medium of claims 1 or 2.

The invention described in claim 4 is a method of selectively detecting Van A and Van B VRE, comprising inoculating a suspension of a testing microorganism to a Van A and Van B VRE detection medium of claims 1 or 2, and incubating the medium at 35-37° C. for 24-48 hours.

The invention described in claim 5 is a method of selectively detecting Van A and Van B VRE, comprising inoculating a specimen to a Van A and Van B VRE detection medium of claims 1 or 2, and incubating the medium at 35-37° C. for 24-48 hours.

DETAILED DESCRIPTION OF THE INVENTION

The present invention is further described as follows;

First of all, vancomycin, D-cycloserine and D-lactic acid used in the present invention are described.

Vancomycin is discovered in 1954 and introduced into clinical usage in 1958. It is a bactericidal glucopeptide antibiotic produced by *Amycolatopsis orientalis* which has a broad spectrum for Gram positive organisms. Since vancomycin has an adverse effect on the kidneys, intestines, etc, it has been used primarily for Gram positive bacteria infection in limited cases for which β-lactam antibiotics can not be used. Vancomycin has begun to attract attention as a therapeutic agent for penicillin resistant *enterococci* infection, pseudomembrane enteritis by *C. difficile* and MRSA which rapidly spread worldwide in the late 1970s, and the drug has become to be used more and more frequently. However, after 1985, *Pediococcus* and *Leuconostoc* infections in immunocompromised patients have been reported in a row. *Pediococcus* and *Leuconostoc* strains had been regarded as nonpathogenic lactic acid bacteria which are naturally resistant to vancomycin. People have been concerned about the emergence of vancomycin resistant bacteria. Usually, vancomycin hydrochloride is white or light yellow crystalline powder and is used as an oral drug. For the present invention, vancomycine hydrochloride is preferably used.

D-cycloserine is white or light yellowish white crystalline powder derived from *Streptomyses garyphalus* and is known as an anti-TB drug that is clinically used for the treatment of pulmonary tuberculosis via oral administration. D-cycloserine has direct effects on ligase that synthesizes D-alanyl-D-alanine which is a part of a cell wall constituting block of bacterial cells in cell wall construction, and inhibits cell wall construction.

In the present invention, commercially available D-lactic acid can be used without problems. Commercially available lactic acid is usually in a racemic modification or its compound, and is widely used in manufacturing soft drinks and confectionery as an acidulant or a preservative. For the present invention, DL-sodium lactate, which is a D-lactic acid compound, is preferably used. DL-sodium lactate provides D-lactic acid in constructing D-alanyl-D-lactic acid which is a cell wall constituting block of VRE.

Next theory of the present invention is described. Because the vancomycin MIC of Van C VRE is 2-32 µg/ml, it is assumed that the concentration of vancomycin to be added to the culture medium should be more than 32 μg/ml to suppress growth. However some of Van B VRE have a low vancomycin MIC which is less than 32 μg/ml. If more than 32 μg/ml of vancomycin is simply added to culture medium, Van B VRE with low vancomycin MIC would be suppressed, resulting in detection miss of said Van B VRE. Hence, the vancomycin concentration for VRE selective media currently used is 6-8 μg/ml and actually cannot be increased further.

The present inventors contemplated that if the MIC of Van B VRE with low vancomycin MIC was able to be increased to more than 32 μg/ml, Van A and Van B VRE was able to be differentiated from Van C VRE by the presence or absence of growth in culture media containing 32 μg/ml of vancomycin. The present inventors paid attention to the resistance mechanism of Van A and Van B VRE. Van A and Van B VRE become vancomycin resistant by replacing D-alanyl-D-alanine with D-alanyl-D-lactic acid. D-alanyl-D-alanine is a part at the penta-peptide end of the cell wall and on which vancomycin has an effect.

Van A VRE, highly resistant to vancomycin, has 8 known vancomycin resistance genes, van R, van S, van H, van A, van X, van Y and van Z. Van H gene produces dehydrogenase and changes pyruvic acid in cells to D-lactic acid. Van A gene binds thus-produced D-lactic acid to D-alanine in cells to produce D-alanyl-D-lactic acid. Thus-produced D-alanyl-D-lactic acid is incorporated into a cell wall component block to form a cell wall which shows resistance to vancomycin.

D-alanyl-D-alanine, a vancomycin target, is continuously produced by ligase which *Enterococci* inherently possess. Thus-produced D-alanyl-D-alanine is degraded by D, D-dipeptidase produced by van X gene or D, D-carboxypeptidase produced by van Y gene to be reconstructed into D-alanyl-D-lactic acid. This series of reactions removes D-alanyl-D-alanine completely and confers Van A VRE high resistance to vancomycin. While Van A VRE shows high resistance to vancomycin, the vancomycin MIC of some of Van B VRE is low. The present inventors assumed that the reason for Van B VRE having low vancomycin MIC might be attributed to two factors.

One of the factors would be D-alanyl-D-alanine left behind. Van B VRE with low vancomycin MIC would have weak activities in reconstructing D-alanyl-D-lactic acid from D-alanyl-D-alanine produced by ligase which *enterococci* inherently possess. Hence D-alanyl-D-alanine, a vancomycin target, would remain and thereby confer Van B VRE low vancomycin MIC.

Another factor would be a lack in D-lactic acid production. Van B VRE with low vancomycin MIC would not produce a sufficient amount of D-lactic acid, which would lead to produce an insufficient amount of D-alanyl-D-lactic acid, and thereby vancomycin MIC lowers relatively.

The present inventors assumed that Van B VRE with low vancomycin MIC would have one of the both factors or both of them. The present inventors thought that if both factors are concurrently removed, the vancomycin MIC of Van B VRE with low MIC would increase, and took following measures to remove those factors.

As a measure to remove D-alanyl-D-alanine left behind, factor 1, D-cycloserine is added to culture medium to suppress D-alanyl-D-alanine production. As described above, D-cycloserine directly acts on ligase which produces D-alanyl-D-alanine (a target of vancmycin), and suppresses the synthesis thereof. As a result D-alanyl-D-alanine synthesis itself is suppressed, leading to relative increase in D-alanyl-D-lactic acid production, resulting in the increased vancomycin MIC.

In other words D-cycloserine may work the same way as van X and van Y genes as mentioned above, to reconstruct D-alanyl-D-lactic acid from D-alanyl-D-alanine. The present inventors made experiments as follows:

TEST EXAMPLE 1

Measurement of vancomycin MIC changes when D-cycloserine is added How the vancomycin MIC of the following enterococcal strains changes was investigated by adding D-cycloserine to culture medium.

Test Strains

In this test, the following strains are used;

| | |
|---|---|
| *Enterococcus faecalis* ATCC29212 that does not carry vancomycin resistance genes | 1 |
| *Enterococcus faecalis* that does not carry vancomycine resistance genes | 3 |
| *Enterococcus faecium* that does not carry vancomycine resistance genes | 3 |
| *Enterococcus avium* that does not carry vancomycine resistance genes | 3 |
| Van C type, *Enterococcus casseliflavus* | 5 |
| Van C type, *Enterococcus gallinarum* | 5 |
| Van A VRE | 5 |
| Van B VRE | 45 |
| A total of 70 strains is investigated. | |

*Enterococcus faecalis* ATCC29212 that does not carry vancomycin resistance genes.

Test Method 96-well microplates are used for measurement. According to the checkerboard method, vancomycin ranging from a final concentration of 0.5-512 μg/ml was placed in 11 columns and D-cycloserine ranging from a final concentration of 1-64 μg/ml was placed in 7 rows.

Brain heart infusion broth was used as a culture medium. Each entrococcal strain was aerobically incubated in brain heart infusion broth at 35° C. for 48 hours and diluted 100-fold with brain heart infusion broth. One hundred μl of the diluted suspension was inoculated in each well. After the microplate was incubated at 35° C. for 18 hours, the vancomycin MIC was determined and the result was shown in Table 1.

Test Results

The addition of D-cycloserine did not change the vancomycin MIC in the following strains and the vancomycin MIC was less than 2 μg/ml.

| | |
|---|---|
| *Enterococcus faecalis* ATCC29212 that does not carry vancomycine resistance genes | 1 |
| *Enterococcus faecalis* that does not carry vancomycine resistance genes | 3 |
| *Enterococcus faecium* that does not carry vancomycine resistance genes | 3 |
| *Enterococcus avium* that does not carry vancomycine resistance genes | 3 |
| The addition of D-cycloserine did not change the vancomycin MIC in the following strains and the vancomycin MIC was less than 16 µg/ml. | |
| Van C type, *Enterococcus casseliflavus* | 5 |
| Van C type, *Enterococcus gallinarum* | 5 |

In contrast, the addition of D-cycloserine increased the vancomycin MIC or maintained the vancomycin MIC as high as more than 512 µg/ml in all of the following strains.

| | |
|---|---|
| Van A VRE | 5 |
| Van B VRE | 45 |

Discussion

The addition of D-cycloserine increased the vancomycin MIC of Van B VRE with low vancomycin MIC. The vancomycin MIC was increased by the addition of D-cycloserine in the concentration ranging from 1 µg/ml to 64 µg/ml and the optimum concentration of addition was confirmed to be at 32 µg/ml.

In the next step, DL-sodium lactate, which is a D-lactic acid compound, was added to culture medium to provide sufficient D-lactic acid for producing D-alanyl-D-lactic acid as a means to supplement an insufficient production of D-lactic acid. The present inventors anticipated that the addition of DL-sodium lactate would produce a sufficient amount of D-alanyl-D-lactic acid, which leads to the increase of D-alanyl-D-lactic acid production relatively, thereby increasing the vancomycin MIC. D-lactic acid presumably has a similar effect as D-lactic acid production by van H gene which was mentioned above. The following study was conducted.

TEST EXAMPLE 2

Measurement of vancomycin MIC changes when D-lactic acid is added.

Changes of the vancomycin MIC of following enterococcal strains were investigated by adding DL-sodium lactate.

Test Strains

In this study, the following strains are used;

| | |
|---|---|
| *Enterococcus faecalis* ATCC29212 that does not carry vancomycine resistance genes | 1 |
| *Enterococcus faecalis* that does not carry vancomycine resistance genes | 3 |
| *Enterococcus faecium* that does not carry vancomycine resistance genes | 3 |
| *Enterococcus avium* that does not carry vancomycine resistance genes | 3 |
| Van C type, *Enterococcus casseliflavus* | 5 |
| Van C type, *Enterococcus gallinarum* | 5 |
| Van A VRE | 5 |
| Van B VRE | 45 |

A total of 70 strains is investigated.

Test Method 96-well microplates are used for measurement. According to the checkerboard method, vancomycin ranging from a final concentration of 0.5-512 µg/ml was placed in 11 columns and DL-sodium lactate ranging from a final concentration of 0.025-1.6 mol/l was placed in 7 rows.

Brain heart infusion broth was used as a culture medium. Each entrococcal strain was aerobically incubated in brain heart infusion broth at 35° C. for 48 hours and diluted 100-fold with brain heart infusion broth. One hundred µl of the diluted suspension was inoculated in each well. After the microplate was incubated at 35° C. for 48 hours, the vancomycin MIC was determined and the result was shown in Table 2.

Test Results

The addition of DL-sodium lactate did not change the vancomycin MIC in the following strains and the vancomycin MIC was less than 2 µg/ml.

| | |
|---|---|
| *Enterococcus faecalis* ATCC29212 that does not carry vancomycine resistance genes | 1 |
| *Enterococcus faecalis* that does not carry vancomycine resistance genes | 3 |
| *Enterococcus faecium* that does not carry vancomycine resistance genes | 3 |
| *Enterococcus avium* that does not carry vancomycine resistance genes | 3 |
| The addition of DL-sodium lactate did not change the vancomycin MIC in the following strains, either and the vancomycin MIC was less than 16 µg/ml. | |
| Van C type, *Enterococcus casseliflavus* | 5 |
| Van C type, *Enterococcus gallinarum* | 5 |

In contrast, the addition of DL-sodium lactate increased the vancomycin MIC or maintained the vancomycin MIC as high as more than 512 µg/ml in all of the following strains.

| | |
|---|---|
| Van A VRE | 5 |
| Van B VRE | 45 |

Discussion

It was confirmed that the addition of DL-sodium lactate increased the vancomycin MIC of Van B VRE with low vancomycin MIC. The vancomycin MIC was increased by the addition of DL-sodium lactate in the concentration ranging from 0.025 to 0.8 mol/l.

However the organisms tend to grow worse in line with the increase of the added amount at the concentration of more than 0.4 mol/l, the optimum concentration of addition was concluded to be at 0.2 mol/l.

From the result of studies 1 and 2, it was confirmed that enterococcal strains not carrying vancomycin resistance genes as well as Van C VRE did not change the vancomycin MIC by adding D-cycloserine or DL-sodium lactate, and their MICs were all less than 32 µg/ml.

On the other hand, it was confirmed that Van A and Van B VRE increased their MIC in all strains by adding D-cycloserine or DL-sodium lactate and their MIC was more than 32 µg/ml.

It is expected that enterococcal strains not carrying vancomycin resistance genes as well as Van C VRE do not grow in culture medium containing more than 32 µg/ml of vancomycin even when the medium is spiked with D-cycloserine and DL-sodium lactate. It is also expected that Van A and Van B VRE grow even in culture medium containing more than 32 µg/ml of vancomycin by adding D-cycloserine and DL-sodium lactate to culture medium. The following studies are conducted.

TEST EXAMPLE 3

Measurement of the growth of VRE in culture medium where D-cycloserine and D-lactic acid are added.

Growth of various enterococcal strains was investigated in culture medium containing D-cycloserine, DL-sodium lactate and vancomycin by dilution-culture test method.

Test Strains

In this study, the following strains are tested;

| | |
|---|---|
| *Enterococcus faecalis* ATCC29212 that does not carry vancomycine resistance genes | 1 |
| *Enterococcus faecalis* that does not carry vancomycine resistance genes | 3 |
| *Enterococcus faecium* that does not carry vancomycine resistance genes | 3 |
| *Enterococcus avium* that does not carry vancomycine resistance genes | 3 |
| Van C type, *Enterococcus casseliflavus* | 5 |
| Van C type, *Enterococcus gallinarum* | 5 |
| Van A VRE | 5 |
| Van B VRE | 45 |
| A total of 70 enterococcal strains is investigated. | |

Test Method

Culture media used are as follows;

1.5% sheep blood agar

2. BHI agar containing 32 μg/ml of vancomycin

3. BHI agar containing 32 μg/ml of vancomycin, 32 μg/ml of D-cycloserine and 0.2 mol/l of DL-sodium lactate Solutions of the above enterococcal strains were prepared to have turbidness of No. 5 MacFarland and the undiluted solution was used to make $10^{-1}$ to $10^{-6}$ dilutions. Ten μl of each of these dilutions were spot-inoculated to each of the above three culture media and aerobically incubated at 35° C. for 48 hours. Colonies grown were counted and compared to the growth on 5% sheep blood agar, which is a control. The results are shown in Table 3, 4 and 5.

In the Tables "+", "++", "+++" and "(+)" mean the following.

| | |
|---|---|
| +++: | more than 10,000 colonies were grown. |
| ++: | 1,001 to 10,000 colonies were grown. |
| +: | 500 to 1,000 colonies were grown. |
| (+): | colonies were observed, but they were very small. |

The above symbols mean the same in Tables 6-8.

Test Results

On BHI agar containing 32 μg/ml of vancomycin as well as BHI agar containing 32 μg/ml of vancomycin, 32 μg/ml of D-cycloserine, and 0.2 mol/l of DL-sodium lactate, the following strains did not grow at all;

| | |
|---|---|
| *Enterococcus faecalis* ATCC29212 that does not carry vancomycine resistance genes | 1 |
| *Enterococcus faecalis* that does not carry vancomycine resistance genes | 3 |
| *Enterococcus faecium* that does not carry vancomycine resistance genes | 3 |
| *Enterococcus avium* that does not carry vancomycine resistance genes | 3 |
| Van C type, *Enterococcus casseliflavus* | 5 |
| Van C type, *Enterococcus gallinarum* | 5 |

On the contrary, all strains of Van A VRE (5 strains) grew as well on both of the BHI agar containing 32 μg/ml of vancomycin and that containing 32 μg/ml of vancomycin, 32 μg/ml of D-cycloserine and 0.2 mol/l of DL-sodium lactate as on 5% sheep blood agar.

For Van B VRE (45 strains), one strain did not grow at all and 12 strains grew extremely poorly on BHI agar containing 32 μg/ml of vancomycin compared to on 5% sheep blood agar. It was considered that these strains were suppressed to grow in the medium containing 32 μg/ml of vancomycin because their vancomycin MIC was low.

Whereas all of the Van B VRE strains grew as well on BHI agar containing 32 μg/ml of vancomycin, 32 μg/ml of D-cycloserine and 0.2 mol/l of DL-sodium lactate as on 5% sheep blood agar. It was considered that Van B VRE with low vancomycin MIC was increased in its vancomycin MIC by adding D-cycloserine and DL-sodium lactate to culture medium so that Van B VRE was able to grow in culture medium containing 32 μg/ml of vancomycin.

Discussion

From the above test results, enterococcal strains not carrying vancomycine resistance genes as well as Van C VRE can be clearly differentiated from Van A and Van B VRE by the presence or absence of growth on BHI agar spiked with 32 μg/ml of vancomycin, 32 μg/ml of D-cycloserine and 0.2 mol/l of DL-sodium lactate.

The present inventors attempted to produce Van A and Van B VRE detection media based on the above studies. The concentration of vancomycin is preferably 32-256 μg/ml and, further, it was concluded that its optimum concentration is 32 μg/ml. The concentration of D-cycloserine is preferably 1-64 μg/ml and, further, it was concluded that its optimum concentration is 32 μg/ml. The concentration of DL-sodium lactate is preferably 0.025-0.8 mol/l and, further, it was concluded that its optimum concentration is 0.2 mol/l.

BHI agar spiked with 20 μg/ml of polymyxin B, 20 μg/ml of aztreonam, 2 μg/ml of amphotericin B and 50 μg/ml of 2,3,5-triphenyltetrazolium chloride (hereinafter referred to as TTC) was used as a medium where VRE can grow. Polymyxin B and aztreonam are added in order to suppress growth of Gram negative bacilli and amphotericin B to suppresses yeast, and TTC is added as a color agent for visualization of VRE colonies. BHI agar containing 20 μg/ml of polymyxin B, 20 μg/ml of aztreonam, 2 μg/ml of amphotericin B and 50 μg/ml of TTC is only one of the medium examples where *enterococci* can grow and is not the essential structural feature of the invention. Any culture media containing ingredient for the growth of *enterococci* can be used in the invention.

The present inventors have successfully produced Van A and Van B VRE detection media including a representative example, namely, BHI agar spiked with 32 μg/ml of vancomycin, 32 μg/ml of D-cycloserine, 0.2 mol/l of DL-sodium lactate, 20 μg/ml of polymyxin B, 20 μg/ml of aztreonam, 2 μg/ml of amphotericin B and 50 μg/ml of TTC.

The present inventors attempted to selectively detect Van A and Van B VRE using a representative example, BHI agar containing 32 μg/ml of vancomycin, 32 μg/ml of D-cycloserine, 0.2 mol/l of DL-sodium lactate, 20 μg/ml of polymyxin B, 20 μg/ml of aztreonam, 2 μg/ml of amphotericin B and 50 μg/ml of TTC. Specifically, Van A and Van B VRE are selectively detected by the following testing procedure.

In a concrete testing procedure when bacteria suspected of Van A and Van B VRE are detected from clinical specimens, the specimens are suspended, inoculated into the Van A and Van B VRE detection media of the present invention, and incubated at 35-37° C. for 24-48 hours. Van A and Van B VRE are selectively detected by the presence or absence of growth.

Alternatively, in another testing procedure where Van A and Van B VRE are directly detected from specimens, specimens are inoculated into the Van A and Van B VRE detection media of the present invention directly and incubated at 35-37° C. for 24-48 hours. Van A and Van B VRE are selectively detected by the presence or absence of growth.

EXAMPLES

Specific procedures are further described in detail in examples.

Example 1

Van A and Van B VRE are selectively detected by inoculating a suspension of testing bacteria into medium Two media, Enterococcosel agar with 8 μg/ml of vancomycin, which is used in the current test method, and BHI agar containing 32 μg/ml of vancomycin, 32 μg/ml of D-cycloserine, 0.2 mol/l of DL-sodium lactate, 20 μg/ml of polymyxin B, 20 μg/ml of aztreonam, 2 μg/ml of amphotericin B and 50 μg/ml of TTC were used for testing growth of various enterococcal strains on dilution media by dilution-culture test method.

Test Strains

In this study, the following strains are tested;

| | |
|---|---|
| *Enterococcus faecalis* ATCC29212 that does not carry vancomycine resistance genes | 1 |
| *Enterococcus faecalis* that does not carry vancomycine resistance genes | 3 |
| *Enterococcus faecium* that does not carry vancomycine resistance genes | 3 |
| *Enterococcus avium* that does not carry vancomycine resistance genes | 3 |
| Van C type, *Enterococcus casseliflavus* | 5 |
| Van C type, *Enterococcus gallinarum* | 5 |
| Van A VRE | 5 |
| Van B VRE | 45 |
| A total of 70 strains is investigated. | |

Test Method

Three media, agar with 5% sheep blood as a control medium, Enterococcosel agar with 8 μg/ml of vancomycin, and BHI agar of the present invention spiked with 32 μg/ml of vancomycin, 32 μg/ml of D-cycloserine, 0.2 mol/l of DL-sodium lactate, 20 μg/ml of polymyxin B, 20 μg/ml of aztreonam, 2 μg/ml of amphotericin B and 50 μg/ml of TTC were used.

Solutions of the above enterococcal strains were prepared to have turbidness of No. 5 MacFarland and the undiluted solution was used to make $10^{-1}$ to $10^{-6}$ dilutions. Ten μl of each of these dilutions were spot-inoculated to each of the above three culture media and aerobically incubated at 35 C for 48 hours. Colonies grown were counted and compared to the growth on 5% sheep blood agar, which is a control. The results are shown in Tables 6, 7 and 8.

Test Results

On Enterococcosel agar with 8 μg/ml of vancomycin and BHI agar spiked with 32 μg/ml of vancomycin, 32 μg/ml of D-cycloserine, 0.2 mol/l of DL-sodium lactate, 20 μg/ml of polymyxin B, 20 μg/ml of aztreonam, 2 μg/ml of amphotericin B and 50 μg/ml of TTC, the following strains did not grow at all;

| | |
|---|---|
| *Enterococcus faecalis* ATCC29212 that does not carry vancomycine resistance genes | 1 |
| *Enterococcus faecalis* that does not carry vancomycine resistance genes | 3 |
| *Enterococcus faecium* that does not carry vancomycine resistance genes | 3 |
| *Enterococcus avium* that does not carry vancomycine resistance genes | 3 |

Van C *Enterococcus casseliflavus* (5 strains) and Van C *Enterococcus gallinarum* (5 strains) were all grown on Enterococcosel agar with 8 μg/ml of vancomycin but were not grown at all on BHI agar spiked with 32 μg/ml of vancomycin, 32 μg/ml of D-cycloserine, 0.2 mol/l of DL-sodium lactate, 20 μg/ml of polymyxin B, 20 μg/ml of aztreonam, 2 μg/ml of amphotericin B and 50 μg/ml of TTC.

Van A VRE (5 strains) grew well on Enterococcosel agar with 8 μg/ml of vancomycin and BHI agar spiked with 32 μg/ml of vancomycin, 32 μg/ml of D-cycloserine, 0.2 mol/l of DL-sodium lactate, 20 μg/ml of polymyxin B, 20 μg/ml of aztreonam, 2 μg/ml of amphotericin B and 50 μg/ml of TTC to the same extent as on agar with 5% sheep blood.

Eight strains of Van B VRE (45 strains) in higher dilution grew poorly on Enterococcosel agar with 8 μg/ml of vancomycin but grew well on BHI agar spiked with 32 μg/ml of vancomycin, 32 μg/ml of D-cycloserine, 0.2 mol/l of DL-sodium lactate, 20 μg/ml of polymyxin B, 20 μg/ml of aztreonam, 2 μg/ml of amphotericin B and 50 μg/ml of TTC to the same extent as on agar with 5% sheep blood.

Discussion

According to the results of Example 1, it is confirmed enterococcal strains not carrying vancomycine resistance genes as well as Van C VRE can be clearly differentiated from Van A and Van B VRE by the presence or absence of growth on BHI agar spiked with 32 μg/ml of vancomycin, 32 μg/ml of D-cycloserine, 0.2 mol/l of DL-sodium lactate, 20 μg/ml of polymyxin B, 20 μg/ml of aztreonam, 2 μg/ml of amphotericin B and 50 μg/ml of TTC. In summary, when Van A and Van B VRE are detected from testing bacteria, they are possible to be selectively detected by the presence or absence of growth on the media after bacteria were suspended, inoculated to Van A and Van B VRE detection media developed by the present inventors, represented by BHI agar spiked with 32 μg/ml of vancomycin, 32 μg/ml of D-cycloserine, 0.2 mol/l of DL-sodium lactate, 20 μg/ml of polymyxin B, 20 μg/ml of aztreonam, 2 μg/ml of amphotericin B and 50 μg/ml of TTC, and incubated for 24-48 hours at 35° C.-37° C.

Example 2

Van A and Van B VRE are selectively detected by directly inoculating specimens to media Two media, Enterococcosel agar with 8 µg/ml of vancomycin, which is used in the current test method, and BHI agar spiked with 32 µg/ml of vancomycin, 32 µg/ml of D-cycloserine, 0.2 mol/l of DL-sodium lactate, 20 µg/ml of polymyxin B, 20 µg/ml of aztreonam, 2 µg/ml of amphotericin B and 50 µg/ml of TTC were used for screening VRE from fecal specimens of patients and compared.

For testing media, 49 fecal specimens of patients were used in this Example.

Test Methods

About an equal amount of sterile physiological saline was added to each of fecal specimens of patients and mixed well. A loopful of resultant paste samples was inoculated to each medium. After 48 hours of incubation at 35° C., colonies grown on plates were carefully examined. Results are shown in Table 9.

Test Results

In 13 specimens of 49 specimens (26.5%), 16 Van C VRE strains were detected on Enterococcosel agar with 8 µg/ml of vancomycin. Conversely, Van C VRE was not detected at all on BHI agar spiked with 32 µg/ml of vancomycin, 32 µg/ml of D-cycloserine, 0.2 mol/l of DL-sodium lactate, 20 µg/ml of polymyxin B, 20 µg/ml of aztreonam, 2 µg/ml of amphotericin B and 50 µg/ml of TTC. Van A and Van B VRE were not detected in any media in this screening test.

Discussion

According to the results of Example 2, it was confirmed that also in actual fecal specimens of patients the growth of Van C VRE was suppressed on Van A and Van B VRE detection media, represented by BHI agar containing 32 µg/ml of vancomycin, 32 µg/ml of D-cycloserine, 0.2 mol/l of DL-sodium lactate, 20 µg/ml of polymyxin B, 20 µg/ml of aztreonam, 2 µg/ml of amphotericin B and 50 µg/ml of TTC.

Known Van B VRE was added to fecal specimens of patients since Van A and Van B VRE were not detected in the screening test of Example 2, and the specimens were tested by the following test to see how many of the added Van B VRE could be detected.

Example 4

Test for confirming the detection rate of Van B VRE from Van B VRE inoculated specimens Testing specimens were 2 patient specimens, Sample 1 and 2, in which Van A and Van B VRE were confirmed not to be present by prior testing, and each of known 3 Van B VRE strains was inoculated to each sample. The inoculating amount of Van B VRE was adjusted to 10-20 cells per 10 µl.

Test Methods

Two media, Enterococcosel agar with 8 µg/ml of vancomycin currently used for a test, and BHI agar spiked with 32 µg/ml of vancomycin, 32 µg/ml of D-cycloserine, 0.2 mol/l of DL-sodium lactate, 20 µg/ml of polymyxin B, 20 µg/ml of aztreonam, 2 µg/ml of amphotericin B and 50 µg/ml of TTC were used. Ten µl of specimens spiked with Van B VRE were inoculated to each medium. After 48 hours of incubation at 35° C., colonies grown on plates were carefully examined. Results are shown in Table 10.

Test Results

In a patient fecal specimen Sample 1, about $10^7$ cells of Van C VRE were present in 10 µl. Van C VRE grew on Enterococcosel agar with 8 µg/ml of vancomycin currently used for a test, which resulted in failing to detect all three strains of Van B VRE. In contrast, Van C VRE was completely suppressed on BHI agar spiked with 32 µg/ml of vancomycin, 32 µg/ml of D-cycloserine, 0.2 mol/l of DL-sodium lactate, 20 µg/ml of polymyxin B, 20 µg/ml of aztreonam, 2 µg/ml of amphotericin B and 50 µg/ml of TTC. It was confirmed that almost same number of cells was detected from the media as that which were inoculated.

Van C VRE did not grow on the media to which Sample 2, a patient fecal specimen, was inoculated. One of three Van B VRE strains was not detected at all on Enterococcosel agar with 8 µg/ml of vancomycin currently used for a test.

Discussion

It was revealed from Sample 1 that Enterococcosel agar with 8 µg/ml of vancomycin currently used for a test might fail to detect Van A and Van B VRE in case specimens contained numerous Van C VRE.

In contrast, it was confirmed that because Van C VRE was completely suppressed, the target bacteria, Van A and Van B VRE, were able to be detected on Van A and Van B VRE detection media of the present invention, even if few of them existed, represented by BHI agar spiked with 32 µg/ml of vancomycin, 32 µg/ml of D-cycloserine, 0.2 mol/l of DL-sodium lactate, 20 µg/ml of polymyxin B, 20 µg/ml of aztreonam, 2 µg/ml of amphotericin B and 50 µg/ml of TTC.

It was evident from Sample 2 that there was Van B VRE which was not detected on Enterococcosel agar with 8 µg/ml of vancomycin currently used for a test when the number of cells was few. In contrast, such Van B VRE grew well and was detected, even if there were few in specimens, on newly developed BHI agar spiked with 32 µg/ml of vancomycin, 32 µg/ml of D-cycloserine, 0.2 mol/l of DL-sodium lactate, 20 µg/ml of polymyxin B, 20 µg/ml of aztreonam, 2 µg/ml of amphotericin B and 50 µg/ml of TTC. Altogether, it is demonstrated from the Test Examples and Examples that Van A and Van B VRE detection media, specifically, represented by BHI agar of the present invention containing 32 µg/ml of vancomycin, 32 µg/ml of D-cycloserine, 0.2 mol/l of DL-sodium lactate, 20 µg/ml of polymyxin B, 20 µg/ml of aztreonam, 2 µg/ml of amphotericin B and 50 µg/ml of TTC can selectively detect clinically important Van A and Van B VRE.

As described above, in a concrete testing procedure when bacteria suspected of Van A and Van B VRE are detected from clinical specimens, the specimens are suspended, inoculated into the Van A and Van B VRE detection media of the present invention, and incubated at 35-37° C. for 24-48 hours. After that it is possible to selectively detect Van A and Van B VRE by the presence or absence of growth.

Alternatively, in another testing procedure where Van A and Van B VRE are directly detected from specimens, specimens are inoculated into the Van A and Van B VRE detection media of the present invention and incubated at 35-37° C. for 24-48 hours. It is possible to selectively detect Van A and Van B VRE by the presence or absence of growth.

INDUSTRIAL APPLICABILITY

Clinically important Van A and Van B VRE are selectively detected from testing microorganisms or specimens using Van A and Van B VRE detection media of the present invention, specifically, represented by BHI agar spiked with 32 µg/ml of vancomycin, 32 µg/ml of D-cycloserine, 0.2 mol/l of DL-sodium lactate, 20 µg/ml of polymyxin B, 20 µg/ml of aztreonam, 2 µg/ml of amphotericin B and 50 µg/ml of TTC. The method for selectively detecting Van A and Van B VRE which was developed newly is markedly simple and increases detection accuracy compared to current detection methods.

Van A and Van B VRE detection media of the present invention and a method of selectively detecting Van A and Van B VRE using the media are very useful in the present medical field where early detection and prevention of infection of Van A and Van B VRE are strongly sought.

TABLE 1

Changes in vancomycin MIC values by adding D-cycloserin (incubated at 35° C. for 48 hours)

| | | | Resistance | vancomycin MIC values(µg/ml) Amount of D-cycloserin added (µg/ml) | | | | | | | |
|---|---|---|---|---|---|---|---|---|---|---|---|
| Seq. | Organism # | Strains | gene | 0 | 1 | 2 | 4 | 8 | 16 | 32 | 64 |
| 1 | E. faecalis ATCC 29212 | E. faecalis | None | 2 | 2 | 2 | 2 | 2 | 2 | 2 | 2 |
| 2 | E. faecalis Control 1 | E. faecalis | None | 2 | 2 | 2 | 2 | 2 | 2 | 2 | 2 |
| 3 | E. faecalis Control 2 | E. faecalis | None | 2 | 2 | 2 | 2 | 2 | 2 | 2 | 2 |
| 4 | E. faecalis Control 3 | E. faecalis | None | 2 | 2 | 2 | 2 | 2 | 2 | 2 | 2 |
| 5 | E. faecium Control 1 | E. faecium | None | 2 | 2 | 1 | 1 | 1 | 1 | 1 | 0.5 |
| 6 | E. faecium Control 2 | E. faecium | None | 1 | 1 | 1 | 1 | 1 | 1 | 1 | 0.5 |
| 7 | E. faecium Control 3 | E. faecium | None | 2 | 2 | 2 | 1 | 2 | 1 | 1 | — |
| 8 | E. avium Control 1 | E. avium | None | 1 | 1 | 1 | 1 | 1 | 1 | 1 | — |
| 9 | E. avium Control 2 | E. avium | None | 2 | 1 | 2 | 1 | 2 | 2 | 1 | — |
| 10 | E. avium Control 3 | E. avium | None | 1 | 1 | 1 | 1 | 1 | 1 | 1 | 0.5 |
| 11 | E. casseliflavus Control 1 | E. casseliflavus | vanC | 8 | 8 | 8 | 8 | 8 | 8 | 8 | 8 |
| 12 | E. casseliflavus Control 2 | E. casseliflavus | vanC | 8 | 8 | 8 | 8 | 8 | 8 | 8 | 8 |
| 13 | E. casseliflavus Control 3 | E. casseliflavus | vanC | 8 | 8 | 8 | 8 | 8 | 8 | 8 | 8 |
| 14 | E. casseliflavus Control 4 | E. casseliflavus | vanC | 8 | 8 | 8 | 8 | 8 | 8 | 8 | 8 |
| 15 | E. casseliflavus Control 5 | E. casseliflavus | vanC | 8 | 8 | 8 | 8 | 8 | 8 | 8 | 8 |
| 16 | E. gallinarum Control 1 | E. gallinarum | vanC | 16 | 16 | 16 | 16 | 16 | 16 | 16 | 16 |
| 17 | E. gallinarum Control 2 | E. gallinarum | vanC | 16 | 16 | 16 | 16 | 16 | 16 | 16 | 16 |
| 18 | E. gallinarum Control 3 | E. gallinarum | vanC | 16 | 16 | 16 | 16 | 16 | 16 | 16 | 16 |
| 19 | E. gallinarum Control 4 | E. gallinarum | vanC | 16 | 16 | 16 | 16 | 16 | 16 | 16 | 16 |
| 20 | E. gallinarum Control 5 | E. gallinarum | vanC | 16 | 16 | 16 | 16 | 16 | 16 | 16 | 16 |
| 21 | TW 3491 | E. faecium | vanA | >512 | >512 | >512 | >512 | >512 | >512 | >512 | >512 |
| 22 | TW 4558 | E. faecium | vanA | 256 | 256 | 256 | 256 | 512 | 512 | 512 | — |
| 23 | TW 4559 | E. faecium | vanA | 512 | >512 | >512 | >512 | 512 | 512 | 512 | 512 |
| 24 | TW 4561 | E. faecium | vanA | 512 | 512 | 512 | 512 | 512 | 512 | >512 | 512 |
| 25 | TW 4590 | E. faecium | vanA | >512 | >512 | >512 | >512 | >512 | >512 | >512 | >512 |
| 26 | TW 3492 | E. faecium | vanB | 32 | 32 | 32 | 32 | 64 | 64 | 128 | 128 |
| 27 | TW 4560 | E. faecium | vanB | 64 | 64 | 64 | 64 | 64 | 128 | 128 | 128 |
| 28 | TW 4589 | E. faecalis | vanB | 16 | 16 | 16 | 16 | 16 | 32 | 64 | 64 |
| 29 | TW 5246 | E. faecalis | vanB | 256 | 512 | 512 | 512 | 512 | 512 | 512 | >512 |
| 30 | TW 5247 | E. faecium | vanB | 16 | 64 | 64 | 128 | 128 | 256 | 256 | 2 |
| 31 | TW 5604 | E. faecium | vanB | 8 | 8 | 16 | 64 | 64 | 64 | 64 | — |
| 32 | TW 5607 | E. faecium | vanB | 512 | 512 | 512 | 512 | 512 | 512 | 512 | 512 |
| 33 | TW 5608 | E. faecalis | vanB | >512 | >512 | >512 | >512 | >512 | >512 | >512 | >512 |
| 34 | TW 5609 | E. faecalis | vanB | 128 | 256 | 256 | 256 | 256 | 256 | 256 | 256 |
| 35 | TW 5610 | E. faecalis | vanB | >512 | >512 | >512 | >512 | >512 | >512 | >512 | >512 |
| 36 | TW 5611 | E. faecalis | vanB | 16 | 16 | 16 | 32 | 32 | 64 | 64 | 64 |
| 37 | TW 5645 | E. faecium | vanB | >512 | >512 | >512 | >512 | >512 | >512 | >512 | >512 |
| 38 | TW 5646 | E. faecium | vanB | 512 | 512 | 512 | 512 | 512 | 512 | 512 | 512 |
| 39 | TW 5668 | E. faecium | vanB | 32 | 16 | 32 | 32 | 32 | 32 | 64 | 64 |
| 40 | TW 5669 | E. faecium | vanB | 32 | 32 | 32 | 32 | 64 | 64 | 128 | 128 |
| 41 | TW 5670 | E. faecium | vanB | 32 | 32 | 64 | 64 | 64 | 64 | 64 | 64 |
| 42 | TW 5671 | E. faecium | vanB | 16 | 32 | 32 | 32 | 32 | 64 | 64 | 64 |
| 43 | TW 5672 | E. faecium | vanB | >512 | >512 | >512 | >512 | >512 | >512 | >512 | >512 |
| 44 | TW 5682 | E. faecalis | vanB | >512 | >512 | >512 | >512 | >512 | >512 | >512 | >512 |
| 45 | TW 5683 | E. faecalis | vanB | 128 | 128 | 128 | 128 | 128 | 256 | 256 | 256 |
| 46 | TW 5684 | E. faecalis | vanB | 128 | 256 | 256 | 256 | 256 | 256 | 256 | 256 |
| 47 | TW 5685 | E. faecalis | vanB | >512 | >512 | >512 | >512 | >512 | >512 | >512 | >512 |
| 48 | TW 5686 | E. faecalis | vanB | 512 | 512 | 512 | 512 | 512 | 512 | 512 | 512 |
| 49 | TW 5687 | E. faecalis | vanB | 64 | 64 | 64 | 128 | 128 | 128 | 256 | 256 |
| 50 | TW 5688 | E. faecium | vanB | 64 | 64 | 64 | 64 | 64 | 64 | 64 | 64 |
| 51 | TW 5689 | E. faecium | vanB | 128 | 128 | 128 | 256 | 256 | 256 | 256 | 128 |
| 52 | TW 5690 | E. faecium | vanB | >512 | >512 | >512 | >512 | >512 | >512 | >512 | >512 |
| 53 | TW 6169 | E. faecalis | vanB | 128 | 128 | 128 | 128 | 128 | 128 | 128 | 128 |
| 54 | TW 6170 | E. faecalis | vanB | 16 | 16 | 16 | 16 | 16 | 16 | 32 | 32 |
| 55 | TW 6171 | E. faecium | vanB | 16 | 16 | 16 | 16 | 16 | 16 | 32 | 16 |
| 56 | TW 6172 | E. faecium | vanB | 16 | 16 | 16 | 16 | 16 | 16 | 32 | 16 |
| 57 | TW 6173 | E. faecium | vanB | 256 | 256 | 256 | 512 | 512 | >512 | >512 | >512 |
| 58 | TW 6174 | E. faecium | vanB | 64 | 64 | 64 | 64 | 64 | 128 | 128 | 128 |
| 59 | TW 6175 | E. faecium | vanB | 256 | 128 | 256 | 256 | 256 | 256 | 256 | 128 |
| 60 | TW 6176 | E. faecium | vanB | 256 | 256 | 256 | 256 | 256 | 512 | >512 | >512 |
| 61 | TW 6177 | E. faecalis | vanB | 256 | 256 | 256 | 256 | 256 | 256 | 512 | >512 |
| 62 | TW 6178 | E. faecium | vanB | 256 | 256 | 256 | 256 | 256 | 256 | 256 | 256 |

TABLE 1-continued

Changes in vancomycin MIC values by adding D-cycloserin (incubated at 35° C. for 48 hours)

| | | | Resistance | vancomycin MIC values(μg/ml) Amount of D-cycloserin added (μg/ml) | | | | | | | |
|---|---|---|---|---|---|---|---|---|---|---|---|
| Seq. | Organism # | Strains | gene | 0 | 1 | 2 | 4 | 8 | 16 | 32 | 64 |
| 63 | TW 6179 | E. faecalis | vanB | 32 | 32 | 32 | 32 | 32 | 64 | 64 | 64 |
| 64 | TW 6180 | E. faecium | vanB | >512 | >512 | >512 | >512 | >512 | >512 | >512 | >512 |
| 65 | TW 6181 | E. faecium | vanB | >512 | >512 | >512 | >512 | >512 | >512 | >512 | >512 |
| 66 | TW 6183 | E. faecalis | vanB | 256 | 256 | 256 | 256 | 256 | 256 | 256 | 128 |
| 67 | TW 6184 | E. faecalis | vanB | >512 | >512 | >512 | >512 | >512 | >512 | >512 | >512 |
| 68 | TW 6185 | E. faecium | vanB | 128 | 128 | 256 | 256 | 256 | 256 | 512 | >512 |
| 69 | TW 7515 | E. faecalis | vanB | 64 | 64 | 128 | 128 | 128 | 128 | 256 | 256 |
| 70 | TW 7516 | E. faecalis | vanB | 512 | 512 | 512 | 512 | 512 | >512 | >512 | >512 |

TABLE 2

Changes in vancomycin MIC values by adding DL-sodium lactate (incubated at 35° C. for 48 hours)

| | | | Resistance | vancomycin MIC values(μg/ml) Amount of DL-Sodium lactate added (mol/l) | | | | | | | |
|---|---|---|---|---|---|---|---|---|---|---|---|
| Sec. | Organism # | Strains | gene | 0 | 0.025 | 0.05 | 0.1 | 0.2 | 0.4 | 0.8 | 1.6 |
| 1 | E. faecalis ATCC 29212 | E. faecalis | None | 2 | 2 | 2 | 2 | 2 | 2 | 2 | 1 |
| 2 | E. faecalis Control 1 | E. faecalis | None | 1 | 2 | 2 | 2 | 2 | 2 | 2 | — |
| 3 | E. faecalis Control 2 | E. faecalis | None | 2 | 2 | 2 | 2 | 2 | 2 | 2 | 0.5 |
| 4 | E. faecalis Control 3 | E. faecalis | None | 1 | 2 | 2 | 2 | 2 | 2 | 2 | 1 |
| 5 | E. faecium Control 1 | E. faecium | None | 1 | 1 | 1 | 2 | 2 | 2 | 2 | 1 |
| 6 | E. faecium Control 2 | E. faecium | None | 1 | 1 | 1 | 2 | 2 | 2 | 2 | 2 |
| 7 | E. faecium Control 3 | E. faecium | None | 1 | 1 | 2 | 2 | 2 | 2 | 2 | 2 |
| 8 | E. avium Control 1 | E. avium | None | 1 | 1 | 1 | 1 | 2 | 2 | 2 | — |
| 9 | E. avium Control 2 | E. avium | None | 2 | 1 | 2 | 2 | 2 | 2 | 2 | — |
| 10 | E. avium Control 3 | E. avium | None | 1 | 1 | 1 | 2 | 2 | 2 | 2 | — |
| 11 | E. casseliflavus Control 1 | E. casseliflavus | vanC | 8 | 8 | 8 | 8 | 16 | 16 | 16 | — |
| 12 | E. casseliflavus Control 2 | E. casseliflavus | vanC | 8 | 8 | 8 | 8 | 16 | 16 | 16 | — |
| 13 | E. casseliflavus Control 3 | E. casseliflavus | vanC | 8 | 8 | 8 | 16 | 16 | 16 | 16 | — |
| 14 | E. casseliflavus Control 4 | E. casseliflavus | vanC | 8 | 8 | 8 | 8 | 16 | 16 | 16 | — |
| 15 | E. casseliflavus Control 5 | E. casseliflavus | vanC | 8 | 8 | 8 | 8 | 16 | 16 | 16 | — |
| 16 | E. gallinarum Control 1 | E. gallinarum | vanC | 8 | 8 | 8 | 8 | 16 | 16 | 16 | — |
| 17 | E. gallinarum Control 2 | E. gallinarum | vanC | 8 | 8 | 16 | 16 | 16 | 16 | 16 | — |
| 18 | E. gallinarum Control 3 | E. gallinarum | vanC | 16 | 8 | 16 | 16 | 16 | 16 | 16 | — |
| 19 | E. gallinarum Control 4 | E. gallinarum | vanC | 8 | 8 | 8 | 16 | 16 | 16 | 16 | — |
| 20 | E. gallinarum Control 5 | E. gallinarum | vanC | 8 | 8 | 8 | 8 | 16 | 16 | 16 | — |
| 21 | TW 3491 | E. faecium | vanA | >512 | >512 | >512 | >512 | >512 | >512 | >512 | >512 |
| 22 | TW 4558 | E. faecium | vanA | 256 | 256 | 512 | 512 | 512 | 512 | 512 | 16 |
| 23 | TW 4559 | E. faecium | vanA | >512 | >512 | >512 | >512 | >512 | >512 | >512 | — |
| 24 | TW 4561 | E. faecium | vanA | 512 | 512 | 512 | 512 | 512 | >512 | >512 | — |
| 25 | TW 4590 | E. faecium | vanA | 512 | >512 | >512 | >512 | >512 | >512 | >512 | — |
| 26 | TW 3492 | E. faecium | vanB | 32 | 64 | 64 | 128 | 256 | 512 | 256 | — |
| 27 | TW 4560 | E. faecium | vanB | 32 | 64 | 128 | 128 | 256 | >512 | >512 | — |
| 28 | TW 4589 | E. faecalis | vanB | 16 | 256 | 512 | >512 | >512 | >512 | >512 | — |
| 29 | TW 5246 | E. faecalis | vanB | 256 | 512 | 512 | 512 | >512 | >512 | >512 | — |
| 30 | TW 5247 | E. faecium | vanB | 16 | 64 | 128 | 128 | 256 | >512 | >512 | 64 |
| 31 | TW 5604 | E. faecium | vanB | 8 | 32 | 64 | 64 | 128 | 512 | >512 | — |
| 32 | TW 5607 | E. faecium | vanB | 512 | 512 | 512 | 512 | >512 | >512 | >512 | — |
| 33 | TW 5608 | E. faecalis | vanB | >512 | >512 | >512 | >512 | >512 | >512 | >512 | — |
| 34 | TW 5609 | E. faecium | vanB | 128 | 512 | 512 | 512 | 512 | 512 | 512 | — |
| 35 | TW 5610 | E. faecalis | vanB | >512 | >512 | >512 | >512 | >512 | >512 | >512 | — |
| 36 | TW 5611 | E. faecalis | vanB | 16 | 64 | 64 | 128 | 256 | 512 | 512 | — |
| 37 | TW 5645 | E. faecium | vanB | 512 | >512 | >512 | >512 | >512 | >512 | >512 | — |
| 38 | TW 5646 | E. faecium | vanB | 256 | 512 | 512 | >512 | >512 | >512 | >512 | — |
| 39 | TW 5668 | E. faecium | vanB | 16 | 32 | 32 | 64 | 64 | 128 | 128 | — |
| 40 | TW 5669 | E. faecium | vanB | 64 | 64 | 64 | 128 | 256 | 256 | 512 | — |
| 41 | TW 5670 | E. faecium | vanB | 32 | 32 | 32 | 64 | 64 | 128 | 512 | — |
| 42 | TW 5671 | E. faecium | vanB | 16 | 16 | 16 | 32 | 64 | 128 | 256 | — |
| 43 | TW 5672 | E. faecium | vanB | >512 | >512 | >512 | >512 | >512 | >512 | >512 | — |
| 44 | TW 5682 | E. faecalis | vanB | >512 | >512 | >512 | >512 | >512 | >512 | >512 | — |
| 45 | TW 5683 | E. faecalis | vanB | 64 | 256 | 512 | 512 | >512 | >512 | >512 | — |
| 46 | TW 5684 | E. faecalis | vanB | 128 | 512 | 512 | 512 | >512 | >512 | >512 | — |
| 47 | TW 5685 | E. faecalis | vanB | 512 | >512 | >512 | >512 | >512 | >512 | >512 | — |
| 48 | TW 5686 | E. faecalis | vanB | 512 | 512 | 512 | >512 | >512 | >512 | >512 | — |
| 49 | TW 5687 | E. faecalis | vanB | 128 | 512 | >512 | >512 | >512 | >512 | >512 | — |
| 50 | TW 5688 | E. faecium | vanB | 64 | 64 | 64 | 128 | 256 | 512 | 512 | — |
| 51 | TW 5689 | E. faecium | vanB | 128 | 128 | 256 | 256 | 512 | >512 | >512 | — |

TABLE 2-continued

Changes in vancomycin MIC values by adding DL-sodium lactate (incubated at 35° C. for 48 hours)

| | | | Resistance | vancomycin MIC values(μg/ml) Amount of DL-Sodium lactate added (mol/l) | | | | | | | |
|---|---|---|---|---|---|---|---|---|---|---|---|
| Sec. | Organism # | Strains | gene | 0 | 0.025 | 0.05 | 0.1 | 0.2 | 0.4 | 0.8 | 1.6 |
| 52 | TW 5690 | E. faecium | vanB | >512 | >512 | >512 | >512 | >512 | >512 | >512 | — |
| 53 | TW 6169 | E. faecalis | vanB | 64 | 128 | 256 | 256 | 256 | >512 | >512 | — |
| 54 | TW 6170 | E. faecalis | vanB | 16 | 32 | 64 | 64 | 128 | 128 | 256 | — |
| 55 | TW 6171 | E. faecium | vanB | 8 | 16 | 16 | 32 | 64 | 128 | 256 | — |
| 56 | TW 6172 | E. faecium | vanB | 8 | 16 | 32 | 32 | 64 | 128 | 128 | — |
| 57 | TW 6173 | E. faecium | vanB | 512 | 512 | >512 | >512 | >512 | >512 | >512 | — |
| 58 | TW 6174 | E. faecium | vanB | 64 | 64 | 128 | 256 | 256 | >512 | >512 | — |
| 59 | TW 6175 | E. faecium | vanB | 128 | 128 | 256 | 256 | 256 | 512 | >512 | — |
| 60 | TW 6176 | E. faecium | vanB | 256 | 256 | 512 | 512 | >512 | >512 | >512 | — |
| 61 | TW 6177 | E. faecalis | vanB | 256 | 256 | 256 | 512 | >512 | >512 | >512 | — |
| 62 | TW 6178 | E. faecium | vanB | 256 | 512 | 512 | 512 | >512 | >512 | >512 | — |
| 63 | TW 6179 | E. faecalis | vanB | 32 | 64 | 64 | 64 | 128 | 256 | 512 | — |
| 64 | TW 6180 | E. faecium | vanB | >512 | >512 | >512 | >512 | >512 | >512 | >512 | — |
| 65 | TW 6181 | E. faecium | vanB | >512 | >512 | >512 | >512 | >512 | >512 | >512 | — |
| 66 | TW 6183 | E. faecium | vanB | 128 | 256 | 512 | 512 | 512 | >512 | >512 | — |
| 67 | TW 6184 | E. faecalis | vanB | >512 | >512 | >512 | >512 | >512 | >512 | >512 | — |
| 68 | TW 6185 | E. faecium | vanB | 128 | 128 | 128 | 128 | 128 | >512 | >512 | — |
| 69 | TW 7515 | E. faecalis | vanB | 64 | 256 | 512 | 512 | >512 | >512 | >512 | — |
| 70 | TW 7516 | E. faecalis | vanB | 256 | >512 | >512 | >512 | >512 | >512 | >512 | — |

TABLE 3

Number of colony growth on each medium in a dilution culture test (incubated at 35° C. for 48 hours)

| | | | | 5% sheep blood agar Dilution | | | | | | | |
|---|---|---|---|---|---|---|---|---|---|---|---|
| Seq. | Organism # | Strains | Resistance gene | Undiluted solution | ×10⁻¹ | ×10⁻² | ×10⁻³ | ×10⁻⁴ | ×10⁻⁵ | ×10⁻⁶ |
| 1 | E. faecalis ATCC 29212 | E. faecalis | None | +++ | +++ | ++ | + | 15 | 0 | 0 |
| 2 | E. faecalis Control 1 | E. faecalis | None | +++ | +++ | ++ | + | 33 | 3 | 0 |
| 3 | E. faecalis Control 2 | E. faecalis | None | +++ | +++ | ++ | + | 21 | 1 | 0 |
| 4 | E. faecalis Control 3 | E. faecalis | None | +++ | +++ | ++ | + | 31 | 5 | 0 |
| 5 | E. faecium Control 1 | E. faecium | None | +++ | +++ | ++ | + | 42 | 5 | 0 |
| 6 | E. faecium Control 2 | E. faecium | None | +++ | +++ | ++ | + | 30 | 1 | 0 |
| 7 | E. faecium Control 3 | E. faecium | None | +++ | +++ | ++ | + | 25 | 1 | 0 |
| 8 | E. avium Control 1 | E. avium | None | +++ | +++ | ++ | + | 22 | 2 | 0 |
| 9 | E. avium Control 2 | E. avium | None | +++ | +++ | ++ | + | 31 | 2 | 0 |
| 10 | E. avium Control 3 | E. avium | None | +++ | +++ | ++ | + | 26 | 1 | 0 |
| 11 | E. casseliflavus Control 1 | E. casseliflavus | vanC | +++ | +++ | ++ | + | 40 | 5 | 0 |
| 12 | E. casseliflavus Control 2 | E. casseliflavus | vanC | +++ | +++ | ++ | + | 36 | 2 | 0 |
| 13 | E. casseliflavus Control 3 | E. casseliflavus | vanC | +++ | +++ | ++ | + | 32 | 2 | 0 |
| 14 | E. casseliflavus Control 4 | E. casseliflavus | vanC | +++ | +++ | ++ | + | 51 | 4 | 0 |
| 15 | E. casseliflavus Control 5 | E. casseliflavus | vanC | +++ | +++ | ++ | + | 46 | 3 | 0 |
| 16 | E. gallinarum Control 1 | E. gallinarum | vanC | +++ | +++ | ++ | + | 28 | 1 | 0 |
| 17 | E. gallinarum Control 2 | E. gallinarum | vanC | +++ | +++ | ++ | + | 41 | 5 | 0 |
| 18 | E. gallinarum Control 3 | E. gallinarum | vanC | +++ | +++ | ++ | + | 47 | 5 | 0 |
| 19 | E. gallinarum Control 4 | E. gallinarum | vanC | +++ | +++ | ++ | + | 50 | 5 | 0 |
| 20 | E. gallinarum Control 5 | E. gallinarum | vanC | +++ | +++ | ++ | + | 38 | 2 | 0 |
| 21 | TW 3491 | E. faecium | vanA | +++ | +++ | ++ | + | 58 | 7 | 0 |
| 22 | TW 4558 | E. faecium | vanA | +++ | +++ | ++ | + | 68 | 7 | 0 |
| 23 | TW 4559 | E. faecium | vanA | +++ | +++ | ++ | + | 59 | 7 | 0 |
| 24 | TW 4561 | E. faecium | vanA | +++ | +++ | ++ | + | 31 | 6 | 0 |
| 25 | TW 4590 | E. faecium | vanA | +++ | +++ | ++ | + | 66 | 6 | 0 |
| 26 | TW 3492 | E. faecium | vanB | +++ | +++ | ++ | + | 74 | 4 | 2 |
| 27 | TW 4560 | E. faecium | vanB | +++ | +++ | ++ | + | 29 | 3 | 0 |
| 28 | TW 4589 | E. faecalis | vanB | +++ | +++ | ++ | + | 34 | 2 | 1 |
| 29 | TW 5246 | E. faecalis | vanB | +++ | +++ | ++ | + | 39 | 4 | 0 |
| 30 | TW 5247 | E. faecium | vanB | +++ | +++ | ++ | + | 34 | 4 | 0 |
| 31 | TW 5604 | E. faecium | vanB | +++ | +++ | ++ | + | 71 | 10 | 1 |
| 32 | TW 5607 | E. faecium | vanB | +++ | +++ | ++ | + | 28 | 1 | 0 |
| 33 | TW 5608 | E. faecalis | vanB | +++ | +++ | ++ | + | 13 | 2 | 0 |
| 34 | TW 5609 | E. faecalis | vanB | +++ | +++ | ++ | + | 30 | 5 | 0 |
| 35 | TW 5610 | E. faecalis | vanB | +++ | ++ | + | 34 | 7 | 0 | 0 |
| 36 | TW 5611 | E. faecalis | vanB | +++ | +++ | ++ | + | 26 | 4 | 0 |
| 37 | TW 5645 | E. faecium | vanB | +++ | +++ | ++ | + | 38 | 5 | 0 |
| 38 | TW 5646 | E. faecium | vanB | +++ | +++ | ++ | + | 22 | 3 | 0 |
| 39 | TW 5668 | E. faecium | vanB | +++ | +++ | ++ | + | 66 | 5 | 0 |

TABLE 3-continued

Number of colony growth on each medium in a dilution culture test (incubated at 35° C. for 48 hours)

| | | | | | 5% sheep blood agar Dilution | | | | | | |
|---|---|---|---|---|---|---|---|---|---|---|---|
| Seq. | Organism # | Strains | Resistance gene | Undiluted solution | $\times 10^{-1}$ | $\times 10^{-2}$ | $\times 10^{-3}$ | $\times 10^{-4}$ | $\times 10^{-5}$ | $\times 10^{-6}$ | |
| 40 | TW 5669 | E. faecium | vanB | +++ | +++ | ++ | + | 71 | 3 | 1 | |
| 41 | TW 5670 | E. faecium | vanB | +++ | +++ | ++ | + | 47 | 5 | 0 | |
| 42 | TW 5671 | E. faecium | vanB | +++ | +++ | ++ | ++ | + | 11 | 0 | |
| 43 | TW 5672 | E. faecium | vanB | +++ | +++ | ++ | + | 39 | 9 | 5 | |
| 44 | TW 5682 | E. faecalis | vanB | +++ | +++ | +++ | ++ | + | 16 | 3 | |
| 45 | TW 5683 | E. faecalis | vanB | +++ | +++ | ++ | + | 54 | 8 | 1 | |
| 46 | TW 5684 | E. faecalis | vanB | +++ | +++ | +++ | ++ | + | 16 | 3 | |
| 47 | TW 5685 | E. faecalis | vanB | +++ | +++ | ++ | + | 22 | 5 | 0 | |
| 48 | TW 5686 | E. faecalis | vanB | +++ | +++ | +++ | ++ | + | 14 | 4 | |
| 49 | TW 5687 | E. faecalis | vanB | +++ | +++ | ++ | + | 28 | 3 | 0 | |
| 50 | TW 5688 | E. faecium | vanB | +++ | +++ | ++ | + | 49 | 11 | 1 | |
| 51 | TW 5689 | E. faecium | vanB | +++ | +++ | ++ | + | 40 | 1 | 1 | |
| 52 | TW 5690 | E. faecium | vanB | +++ | +++ | +++ | ++ | + | 15 | 2 | |
| 53 | TW 6169 | E. faecalis | vanB | +++ | +++ | +++ | ++ | + | 23 | 16 | |
| 54 | TW 6170 | E. faecalis | vanB | +++ | +++ | ++ | + | 45 | 6 | 1 | |
| 55 | TW 6171 | E. faecalis | vanB | +++ | +++ | +++ | ++ | + | 8 | 1 | |
| 56 | TW 6172 | E. faecium | vanB | +++ | +++ | ++ | + | 30 | 8 | 1 | |
| 57 | TW 6173 | E. faecium | vanB | +++ | +++ | ++ | ++ | + | 7 | 2 | |
| 58 | TW 6174 | E. faecium | vanB | +++ | +++ | ++ | + | 58 | 6 | 0 | |
| 59 | TW 6175 | E. faecium | vanB | +++ | +++ | ++ | + | 51 | 3 | 0 | |
| 60 | TW 6176 | E. faecium | vanB | +++ | +++ | ++ | + | 42 | 9 | 3 | |
| 61 | TW 6177 | E. faecalis | vanB | +++ | +++ | ++ | + | 52 | 15 | 2 | |
| 62 | TW 6178 | E. faecalis | vanB | +++ | +++ | ++ | + | 25 | 6 | 1 | |
| 63 | TW 6179 | E. faecalis | vanB | +++ | +++ | ++ | + | 53 | 18 | 4 | |
| 64 | TW 6180 | E. faecium | vanB | +++ | +++ | ++ | + | 52 | 4 | 1 | |
| 65 | TW 6181 | E. faecium | vanB | +++ | +++ | ++ | + | 30 | 4 | 0 | |
| 66 | TW 6183 | E. faecalis | vanB | +++ | +++ | ++ | + | 16 | 5 | 2 | |
| 67 | TW 6184 | E. faecalis | vanB | +++ | +++ | ++ | + | 58 | 13 | 3 | |
| 68 | TW 6185 | E. faecalis | vanB | +++ | +++ | ++ | + | 60 | 12 | 3 | |
| 69 | TW 7515 | E. faecalis | vanB | +++ | +++ | +++ | ++ | + | 12 | 1 | |
| 70 | TW 7516 | E. faecalis | vanB | +++ | +++ | ++ | + | 47 | 5 | 2 | |

TABLE 4

Number of colony growth on each medium in a dilution culture test (incubated at 35° C. for 48 hours)

| | | | | | BHI agar with 32 µg/ml of vancomycin Dilution | | | | | | |
|---|---|---|---|---|---|---|---|---|---|---|---|
| Seq. | Organism # | Strains | Resistance gene | Undiluted solution | $\times 10^{-1}$ | $\times 10^{-2}$ | $\times 10^{-3}$ | $\times 10^{-4}$ | $\times 10^{-5}$ | $\times 10^{-6}$ | |
| 1 | E. faecalis ATCC 29212 | E. faecalis | None | 0 | 0 | 0 | 0 | 0 | 0 | 0 | |
| 2 | E. faecalis Control 1 | E. faecalis | None | 0 | 0 | 0 | 0 | 0 | 0 | 0 | |
| 3 | E. faecalis Control 2 | E. faecalis | None | 0 | 0 | 0 | 0 | 0 | 0 | 0 | |
| 4 | E. faecalis Control 3 | E. faecalis | None | 0 | 0 | 0 | 0 | 0 | 0 | 0 | |
| 5 | E. faecium Control 1 | E. faecium | None | 0 | 0 | 0 | 0 | 0 | 0 | 0 | |
| 6 | E. faecium Control 2 | E. faecium | None | 0 | 0 | 0 | 0 | 0 | 0 | 0 | |
| 7 | E. faecium Control 3 | E. faecium | None | 0 | 0 | 0 | 0 | 0 | 0 | 0 | |
| 8 | E. avium Control 1 | E. avium | None | 0 | 0 | 0 | 0 | 0 | 0 | 0 | |
| 9 | E. avium Control 2 | E. avium | None | 0 | 0 | 0 | 0 | 0 | 0 | 0 | |
| 10 | E. avium Control 3 | E. avium | None | 0 | 0 | 0 | 0 | 0 | 0 | 0 | |
| 11 | E. casseliflavus Control 1 | E. casseliflavus | vanC | 0 | 0 | 0 | 0 | 0 | 0 | 0 | |
| 12 | E. casseliflavus Control 2 | E. casseliflavus | vanC | 0 | 0 | 0 | 0 | 0 | 0 | 0 | |
| 13 | E. casseliflavus Control 3 | E. casseliflavus | vanC | 0 | 0 | 0 | 0 | 0 | 0 | 0 | |
| 14 | E. casseliflavus Control 4 | E. casseliflavus | vanC | 0 | 0 | 0 | 0 | 0 | 0 | 0 | |
| 15 | E. casseliflavus Control 5 | E. casseliflavus | vanC | 0 | 0 | 0 | 0 | 0 | 0 | 0 | |
| 16 | E. gallinarum Control 1 | E. gallinarum | vanC | 0 | 0 | 0 | 0 | 0 | 0 | 0 | |
| 17 | E. gallinarum Control 2 | E. gallinarum | vanC | 0 | 0 | 0 | 0 | 0 | 0 | 0 | |
| 18 | E. gallinarum Control 3 | E. gallinarum | vanC | 0 | 0 | 0 | 0 | 0 | 0 | 0 | |
| 19 | E. gallinarum Control 4 | E. gallinarum | vanC | 0 | 0 | 0 | 0 | 0 | 0 | 0 | |
| 20 | E. gallinarum Control 5 | E. gallinarum | vanC | 0 | 0 | 0 | 0 | 0 | 0 | 0 | |
| 21 | TW 3491 | E. faecium | vanA | +++ | +++ | ++ | + | 55 | 5 | 0 | |
| 22 | TW 4558 | E. faecium | vanA | +++ | +++ | ++ | + | 61 | 7 | 0 | |
| 23 | TW 4559 | E. faecium | vanA | +++ | +++ | ++ | + | 49 | 2 | 1 | |
| 24 | TW 4561 | E. faecium | vanA | +++ | +++ | ++ | + | 35 | 2 | 0 | |
| 25 | TW 4590 | E. faecium | vanA | +++ | +++ | ++ | + | 58 | 5 | 0 | |
| 26 | TW 3492 | E. faecium | vanB | +++ | +++ | ++ | + | (44) | 2 | 0 | |

TABLE 4-continued

Number of colony growth on each medium in a dilution culture test (incubated at 35° C. for 48 hours)

| | | | | Resistance | BHI agar with 32 µg/ml of vancomycin Dilution | | | | | | |
|---|---|---|---|---|---|---|---|---|---|---|---|
| Seq. | Organism # | Strains | | gene | Undiluted solution | $\times 10^{-1}$ | $\times 10^{-2}$ | $\times 10^{-3}$ | $\times 10^{-4}$ | $\times 10^{-5}$ | $\times 10^{-6}$ |
| 27 | TW 4560 | *E. faecium* | vanB | +++ | +++ | ++ | + | 22 | 5 | 0 |
| 28 | TW 4589 | *E. faecalis* | vanB | + | 2 | 3 | 1 | 0 | 0 | 0 |
| 29 | TW 5246 | *E. faecalis* | vanB | +++ | +++ | ++ | + | 23 | 5 | 0 |
| 30 | TW 5247 | *E. faecium* | vanB | +++ | ++ | (+) | 0 | 0 | 0 | 0 |
| 31 | TW 5604 | *E. faecium* | vanB | +++ | ++ | (+) | (+) | 0 | 0 | 0 |
| 32 | TW 5607 | *E. faecium* | vanB | +++ | +++ | ++ | + | 28 | 1 | 0 |
| 33 | TW 5608 | *E. faecalis* | vanB | +++ | +++ | ++ | + | 12 | 1 | 0 |
| 34 | TW 5609 | *E. faecalis* | vanB | +++ | +++ | ++ | + | 33 | 2 | 0 |
| 35 | TW 5610 | *E. faecalis* | vanB | +++ | ++ | + | 40 | 4 | 1 | 0 |
| 36 | TW 5611 | *E. faecalis* | vanB | (+) | (+) | (+) | 0 | 0 | 0 | 0 |
| 37 | TW 5645 | *E. faecium* | vanB | +++ | +++ | ++ | + | 36 | 5 | 0 |
| 38 | TW 5646 | *E. faecium* | vanB | +++ | +++ | ++ | + | 16 | 2 | 0 |
| 39 | TW 5668 | *E. faecium* | vanB | +++ | + | (+) | 0 | 0 | 0 | 0 |
| 40 | TW 5669 | *E. faecium* | vanB | ++ | (+) | (+) | 0 | 0 | 0 | 0 |
| 41 | TW 5670 | *E. faecium* | vanB | +++ | ++ | (+) | 0 | 0 | 0 | 0 |
| 42 | TW 5671 | *E. faecium* | vanB | +++ | ++ | (+) | 0 | 0 | 0 | 0 |
| 43 | TW 5672 | *E. faecium* | vanB | +++ | +++ | ++ | + | 43 | 6 | 0 |
| 44 | TW 5682 | *E. faecalis* | vanB | +++ | +++ | ++ | ++ | + | 28 | 5 |
| 45 | TW 5683 | *E. faecalis* | vanB | +++ | +++ | ++ | + | 30 | 6 | 5 |
| 46 | TW 5684 | *E. faecalis* | vanB | +++ | +++ | ++ | + | 72 | 18 | 1 |
| 47 | TW 5685 | *E. faecalis* | vanB | +++ | +++ | ++ | + | 14 | 3 | 0 |
| 48 | TW 5686 | *E. faecalis* | vanB | +++ | +++ | ++ | + | 68 | 19 | 1 |
| 49 | TW 5687 | *E. faecalis* | vanB | +++ | +++ | ++ | + | 23 | 7 | 0 |
| 50 | TW 5688 | *E. faecium* | vanB | +++ | +++ | ++ | + | 39 | 6 | 2 |
| 51 | TW 5689 | *E. faecium* | vanB | +++ | +++ | ++ | + | 42 | 6 | 0 |
| 52 | TW 5690 | *E. faecium* | vanB | +++ | +++ | +++ | ++ | + | 17 | 1 |
| 53 | TW 6169 | *E. faecalis* | vanB | +++ | +++ | ++ | ++ | + | 19 | 10 |
| 54 | TW 6170 | *E. faecalis* | vanB | 0 | 0 | 0 | 0 | 0 | 0 | 0 |
| 55 | TW 6171 | *E. faecium* | vanB | ++ | (+) | (+) | 1 | 0 | 0 | 0 |
| 56 | TW 6172 | *E. faecium* | vanB | (+) | 0 | 0 | 0 | 0 | 0 | 0 |
| 57 | TW 6173 | *E. faecium* | vanB | +++ | +++ | ++ | + | 47 | 11 | 4 |
| 58 | TW 6174 | *E. faecium* | vanB | +++ | +++ | ++ | + | 40 | 3 | 2 |
| 59 | TW 6175 | *E. faecium* | vanB | +++ | +++ | ++ | + | 56 | 9 | 0 |
| 60 | TW 6176 | *E. faecium* | vanB | +++ | +++ | ++ | + | 36 | 2 | 1 |
| 61 | TW 6177 | *E. faecalis* | vanB | +++ | +++ | ++ | + | 49 | 13 | 1 |
| 62 | TW 6178 | *E. faecium* | vanB | +++ | +++ | ++ | + | 28 | 3 | 1 |
| 63 | TW 6179 | *E. faecalis* | vanB | +++ | ++ | + | 60 | 7 | 2 | 0 |
| 64 | TW 6180 | *E. faecium* | vanB | +++ | +++ | ++ | + | 39 | 10 | 0 |
| 65 | TW 6181 | *E. faecium* | vanB | +++ | +++ | ++ | + | 20 | 3 | 1 |
| 66 | TW 6183 | *E. faecalis* | vanB | +++ | +++ | ++ | + | 15 | 5 | 1 |
| 67 | TW 6184 | *E. faecalis* | vanB | +++ | +++ | ++ | + | 52 | 11 | 2 |
| 68 | TW 6185 | *E. faecium* | vanB | +++ | +++ | ++ | (+) | 0 | 5 | 0 |
| 69 | TW 7515 | *E. faecalis* | vanB | +++ | +++ | ++ | + | 32 | 3 | 0 |
| 70 | TW 7516 | *E. faecalis* | vanB | +++ | +++ | ++ | + | 46 | 2 | 0 |

TABLE 5

Number of colony growth on each medium in a dilution culture test (incubated at 35° C. for 48 hours)

| | | | Resistance | BHI agar with 32 µg/ml of vancomycin, 32 µg/ml of D-cycloserine, and 0.2 mol/l of sodium lactate Dilution | | | | | | |
|---|---|---|---|---|---|---|---|---|---|---|
| Seq. | Organism # | Strains | gene | Undiluted solution | $\times 10^{-1}$ | $\times 10^{-2}$ | $\times 10^{-3}$ | $\times 10^{-4}$ | $\times 10^{-5}$ | $\times 10^{-6}$ |
| 1 | *E. faecalis* ATCC 29212 | *E. faecalis* | None | 0 | 0 | 0 | 0 | 0 | 0 | 0 |
| 2 | *E. faecalis* Control 1 | *E. faecalis* | None | 0 | 0 | 0 | 0 | 0 | 0 | 0 |
| 3 | *E. faecalis* Control 2 | *E. faecalis* | None | 0 | 0 | 0 | 0 | 0 | 0 | 0 |
| 4 | *E. faecalis* Control 3 | *E. faecalis* | None | 0 | 0 | 0 | 0 | 0 | 0 | 0 |
| 5 | *E. faecium* Control 1 | *E. faecium* | None | 0 | 0 | 0 | 0 | 0 | 0 | 0 |
| 6 | *E. faecium* Control 2 | *E. faecium* | None | 0 | 0 | 0 | 0 | 0 | 0 | 0 |
| 7 | *E. faecium* Control 3 | *E. faecium* | None | 0 | 0 | 0 | 0 | 0 | 0 | 0 |
| 8 | *E. avium* Control 1 | *E. avium* | None | 0 | 0 | 0 | 0 | 0 | 0 | 0 |
| 9 | *E. avium* Control 2 | *E. avium* | None | 0 | 0 | 0 | 0 | 0 | 0 | 0 |
| 10 | *E. avium* Control 3 | *E. avium* | None | 0 | 0 | 0 | 0 | 0 | 0 | 0 |
| 11 | *E. casseliflavus* Control 1 | *E. casseliflavus* | vanC | 0 | 0 | 0 | 0 | 0 | 0 | 0 |
| 12 | *E. casseliflavus* Control 2 | *E. casseliflavus* | vanC | 0 | 0 | 0 | 0 | 0 | 0 | 0 |

TABLE 5-continued

Number of colony growth on each medium in a dilution culture test (incubated at 35° C. for 48 hours)

|  |  |  |  | BHI agar with 32 µg/ml of vancomycin, 32 µg/ml of D-cycloserine, and 0.2 mol/l of sodium lactate Dilution | | | | | | |
|---|---|---|---|---|---|---|---|---|---|---|
| Seq. | Organism # | Strains | Resistance gene | Undiluted solution | ×10⁻¹ | ×10⁻² | ×10⁻³ | ×10⁻⁴ | ×10⁻⁵ | ×10⁻⁶ |
| 13 | *E. casseliflavus* Control 3 | *E. casseliflavus* | vanC | 0 | 0 | 0 | 0 | 0 | 0 | 0 |
| 14 | *E. casseliflavus* Control 4 | *E. casseliflavus* | vanC | 0 | 0 | 0 | 0 | 0 | 0 | 0 |
| 15 | *E. casseliflavus* Control 5 | *E. casseliflavus* | vanC | 0 | 0 | 0 | 0 | 0 | 0 | 0 |
| 16 | *E. gallinarum* Control 1 | *E. gallinarum* | vanC | 0 | 0 | 0 | 0 | 0 | 0 | 0 |
| 17 | *E. gallinarum* Control 2 | *E. gallinarum* | vanC | 0 | 0 | 0 | 0 | 0 | 0 | 0 |
| 18 | *E. gallinarum* Control 3 | *E. gallinarum* | vanC | 0 | 0 | 0 | 0 | 0 | 0 | 0 |
| 19 | *E. gallinarum* Control 4 | *E. gallinarum* | vanC | 0 | 0 | 0 | 0 | 0 | 0 | 0 |
| 20 | *E. gallinarum* Control 5 | *E. gallinarum* | vanC | 0 | 0 | 0 | 0 | 0 | 0 | 0 |
| 21 | TW 3491 | *E. faecium* | vanA | +++ | +++ | ++ | + | 62 | 8 | 1 |
| 22 | TW 4558 | *E. faecium* | vanA | +++ | +++ | ++ | + | 66 | 9 | 1 |
| 23 | TW 4559 | *E. faecium* | vanA | +++ | +++ | ++ | + | 60 | 5 | 0 |
| 24 | TW 4561 | *E. faecium* | vanA | +++ | +++ | ++ | + | 41 | 6 | 0 |
| 25 | TW 4590 | *E. faecium* | vanA | +++ | +++ | ++ | + | 68 | 5 | 0 |
| 26 | TW 3492 | *E. faecium* | vanB | +++ | +++ | ++ | + | 46 | 10 | 2 |
| 27 | TW 4560 | *E. faecium* | vanB | +++ | +++ | ++ | + | 26 | 4 | 0 |
| 28 | TW 4589 | *E. faecalis* | vanB | +++ | +++ | ++ | + | 22 | 2 | 0 |
| 29 | TW 5246 | *E. faecalis* | vanB | +++ | +++ | ++ | + | 22 | 3 | 0 |
| 30 | TW 5247 | *E. faecium* | vanB | +++ | +++ | ++ | + | 36 | 3 | 0 |
| 31 | TW 5604 | *E. faecium* | vanB | +++ | +++ | ++ | + | 59 | 5 | 1 |
| 32 | TW 5607 | *E. faecium* | vanB | +++ | +++ | ++ | + | 24 | 4 | 0 |
| 33 | TW 5608 | *E. faecalis* | vanB | +++ | +++ | ++ | + | 14 | 1 | 0 |
| 34 | TW 5609 | *E. faecalis* | vanB | +++ | +++ | ++ | + | 28 | 0 | 0 |
| 35 | TW 5610 | *E. faecalis* | vanB | +++ | ++ | + | 34 | 8 | 0 | 0 |
| 36 | TW 5611 | *E. faecalis* | vanB | +++ | +++ | ++ | + | 37 | 0 | 0 |
| 37 | TW 5645 | *E. faecium* | vanB | +++ | +++ | ++ | + | 43 | 3 | 1 |
| 38 | TW 5646 | *E. faecium* | vanB | +++ | +++ | ++ | + | 23 | 2 | 1 |
| 39 | TW 5668 | *E. faecium* | vanB | +++ | +++ | ++ | + | 40 | 2 | 0 |
| 40 | TW 5669 | *E. faecium* | vanB | +++ | +++ | ++ | + | 46 | 2 | 0 |
| 41 | TW 5670 | *E. faecium* | vanB | +++ | +++ | ++ | + | 44 | 7 | 0 |
| 42 | TW 5671 | *E. faecium* | vanB | +++ | +++ | ++ | + | 27 | 6 | 0 |
| 43 | TW 5672 | *E. faecium* | vanB | +++ | +++ | ++ | + | 32 | 9 | 3 |
| 44 | TW 5682 | *E. faecalis* | vanB | +++ | +++ | +++ | ++ | + | 18 | 2 |
| 45 | TW 5683 | *E. faecalis* | vanB | +++ | +++ | ++ | + | 40 | 9 | 6 |
| 46 | TW 5684 | *E. faecalis* | vanB | +++ | +++ | ++ | + | 58 | 11 | 4 |
| 47 | TW 5685 | *E. faecalis* | vanB | +++ | +++ | ++ | + | 27 | 6 | 0 |
| 48 | TW 5686 | *E. faecalis* | vanB | +++ | +++ | ++ | + | 47 | 12 | 2 |
| 49 | TW 5687 | *E. faecalis* | vanB | +++ | +++ | ++ | + | 30 | 4 | 1 |
| 50 | TW 5688 | *E. faecium* | vanB | +++ | +++ | ++ | + | 42 | 7 | 2 |
| 51 | TW 5689 | *E. faecium* | vanB | +++ | +++ | ++ | + | 26 | 3 | 0 |
| 52 | TW 5690 | *E. faecium* | vanB | +++ | +++ | ++ | + | 111 | 11 | 2 |
| 53 | TW 6169 | *E. faecalis* | vanB | +++ | +++ | +++ | ++ | + | 17 | 7 |
| 54 | TW 6170 | *E. faecalis* | vanB | +++ | +++ | ++ | + | 43 | 4 | 3 |
| 55 | TW 6171 | *E. faecium* | vanB | +++ | +++ | ++ | + | 12 | 2 | 1 |
| 56 | TW 6172 | *E. faecium* | vanB | +++ | +++ | ++ | + | 17 | 6 | 1 |
| 57 | TW 6173 | *E. faecium* | vanB | +++ | +++ | ++ | + | 70 | 2 | 0 |
| 58 | TW 6174 | *E. faecium* | vanB | +++ | +++ | ++ | + | 57 | 13 | 2 |
| 59 | TW 6175 | *E. faecium* | vanB | +++ | +++ | ++ | + | 43 | 8 | 0 |
| 60 | TW 6176 | *E. faecium* | vanB | +++ | +++ | ++ | + | 73 | 9 | 1 |
| 61 | TW 6177 | *E. faecalis* | vanB | +++ | +++ | ++ | + | 43 | 6 | 4 |
| 62 | TW 6178 | *E. faecium* | vanB | +++ | +++ | ++ | + | 37 | 7 | 2 |
| 63 | TW 6179 | *E. faecalis* | vanB | +++ | +++ | ++ | + | 27 | 3 | 2 |
| 64 | TW 6180 | *E. faecium* | vanB | +++ | +++ | ++ | + | 40 | 10 | 1 |
| 65 | TW 6181 | *E. faecium* | vanB | +++ | +++ | ++ | + | 31 | 2 | 0 |
| 66 | TW 6183 | *E. faecalis* | vanB | +++ | +++ | ++ | + | 17 | 2 | 1 |
| 67 | TW 6184 | *E. faecalis* | vanB | +++ | +++ | ++ | + | 47 | 15 | 4 |
| 68 | TW 6185 | *E. faecium* | vanB | +++ | +++ | ++ | + | 68 | 13 | 8 |
| 69 | TW 7515 | *E. faecalis* | vanB | +++ | +++ | ++ | ++ | + | 6 | 0 |
| 70 | TW 7516 | *E. faecalis* | vanB | +++ | +++ | ++ | + | 46 | 3 | 1 |

TABLE 6

Number of colony growth on each medium in a dilution culture test (incubated at 35° C. for 48 hours)

| | | | | | 5% sheep blood agar Dilution | | | | | | |
|---|---|---|---|---|---|---|---|---|---|---|---|
| Seq. | Organism # | Strains | Resistance gene | Undiluted solution | $\times 10^{-1}$ | $\times 10^{-2}$ | $\times 10^{-3}$ | $\times 10^{-4}$ | $\times 10^{-5}$ | $\times 10^{-6}$ |
| 1 | E. faecalis ATCC 29212 | E. faecalis | None | +++ | +++ | ++ | + | 30 | 4 | 0 |
| 2 | E. faecalis Control 1 | E. faecalis | None | +++ | +++ | ++ | + | 42 | 3 | 0 |
| 3 | E. faecalis Control 2 | E. faecalis | None | +++ | +++ | ++ | + | 51 | 3 | 0 |
| 4 | E. faecalis Control 3 | E. faecalis | None | +++ | +++ | ++ | + | 38 | 1 | 0 |
| 5 | E. faecium Control 1 | E. faecium | None | +++ | +++ | ++ | + | 29 | 1 | 0 |
| 6 | E. faecium Control 2 | E. faecium | None | +++ | +++ | ++ | + | 40 | 5 | 0 |
| 7 | E. faecium Control 3 | E. faecium | None | +++ | +++ | ++ | + | 38 | 5 | 0 |
| 8 | E. avium Control 1 | E. avium | None | +++ | +++ | ++ | + | 21 | 1 | 0 |
| 9 | E. avium Control 2 | E. avium | None | +++ | +++ | ++ | + | 38 | 1 | 0 |
| 10 | E. avium Control 3 | E. avium | None | +++ | +++ | ++ | + | 33 | 1 | 0 |
| 11 | E. casseliflavus Control 1 | E. casseliflavus | vanC | +++ | +++ | ++ | + | 44 | 5 | 0 |
| 12 | E. casseliflavus Control 2 | E. casseliflavus | vanC | +++ | +++ | ++ | + | 38 | 5 | 0 |
| 13 | E. casseliflavus Control 3 | E. casseliflavus | vanC | +++ | +++ | ++ | + | 42 | 2 | 0 |
| 14 | E. casseliflavus Control 4 | E. casseliflavus | vanC | +++ | +++ | ++ | + | 50 | 1 | 0 |
| 15 | E. casseliflavus Control 5 | E. casseliflavus | vanC | +++ | +++ | ++ | + | 37 | 1 | 0 |
| 16 | E. gallinarum Control 1 | E. gallinarum | vanC | +++ | +++ | ++ | + | 38 | 4 | 0 |
| 17 | E. gallinarum Control 2 | E. gallinarum | vanC | +++ | +++ | ++ | + | 61 | 7 | 0 |
| 18 | E. gallinarum Control 3 | E. gallinarum | vanC | +++ | +++ | ++ | + | 44 | 8 | 0 |
| 19 | E. gallinarum Control 4 | E. gallinarum | vanC | +++ | +++ | ++ | + | 51 | 4 | 0 |
| 20 | E. gallinarum Control 5 | E. gallinarum | vanC | +++ | +++ | ++ | + | 31 | 1 | 0 |
| 21 | TW 3491 | E. faecium | vanA | +++ | +++ | ++ | + | 60 | 10 | 0 |
| 22 | TW 4558 | E. faecium | vanA | +++ | +++ | ++ | + | 40 | 6 | 0 |
| 23 | TW 4559 | E. faecium | vanA | +++ | +++ | ++ | + | 38 | 2 | 0 |
| 24 | TW 4561 | E. faecium | vanA | +++ | +++ | ++ | + | 51 | 5 | 0 |
| 25 | TW 4590 | E. faecium | vanA | +++ | +++ | ++ | + | 58 | 5 | 0 |
| 26 | TW 3492 | E. faecium | vanB | +++ | +++ | ++ | + | 100 | 13 | 1 |
| 27 | TW 4560 | E. faecium | vanB | +++ | +++ | ++ | + | 100 | 8 | 0 |
| 28 | TW 4589 | E. faecium | vanB | +++ | ++ | + | 100 | 18 | 7 | 0 |
| 29 | TW 5246 | E. faecium | vanB | +++ | ++ | + | 100 | 20 | 7 | 1 |
| 30 | TW 5247 | E. faecium | vanB | +++ | +++ | ++ | + | 70 | 7 | 1 |
| 31 | TW 5604 | E. faecium | vanB | +++ | +++ | ++ | + | 60 | 10 | 1 |
| 32 | TW 5607 | E. faecium | vanB | +++ | +++ | ++ | + | 100 | 19 | 3 |
| 33 | TW 5608 | E. faecalis | vanB | +++ | ++ | + | 80 | 20 | 20 | 1 |
| 34 | TW 5609 | E. faecalis | vanB | +++ | ++ | + | 70 | 8 | 6 | 1 |
| 35 | TW 5610 | E. faecalis | vanB | +++ | ++ | + | 100 | 50 | 50 | 4 |
| 36 | TW 5611 | E. faecalis | vanB | +++ | ++ | + | 100 | 50 | 50 | 8 |
| 37 | TW 5645 | E. faecium | vanB | +++ | +++ | ++ | + | 30 | 10 | 3 |
| 38 | TW 5646 | E. faecium | vanB | +++ | +++ | ++ | + | 40 | 25 | 4 |
| 39 | TW 5668 | E. faecium | vanB | +++ | +++ | ++ | + | 50 | 5 | 1 |
| 40 | TW 5669 | E. faecium | vanB | +++ | +++ | ++ | + | 100 | 9 | 1 |
| 41 | TW 5670 | E. faecium | vanB | +++ | +++ | ++ | + | 70 | 9 | 1 |
| 42 | TW 5671 | E. faecium | vanB | +++ | +++ | ++ | + | 70 | 10 | 3 |
| 43 | TW 5672 | E. faecium | vanB | +++ | +++ | ++ | + | 17 | 1 | 0 |
| 44 | TW 5682 | E. faecalis | vanB | +++ | +++ | ++ | + | 80 | 8 | 0 |
| 45 | TW 5683 | E. faecalis | vanB | +++ | +++ | ++ | + | 60 | 1 | 1 |
| 46 | TW 5684 | E. faecalis | vanB | +++ | +++ | ++ | + | 13 | 6 | 0 |
| 47 | TW 5685 | E. faecalis | vanB | +++ | ++ | + | 40 | 7 | 1 | 0 |
| 48 | TW 5686 | E. faecalis | vanB | +++ | ++ | + | 60 | 8 | 2 | 1 |
| 49 | TW 5687 | E. faecalis | vanB | +++ | + | 100 | 8 | 2 | 0 | 0 |
| 50 | TW 5688 | E. faecium | vanB | +++ | +++ | ++ | + | 30 | 5 | 0 |
| 51 | TW 5689 | E. faecium | vanB | +++ | +++ | ++ | + | 30 | 4 | 2 |
| 52 | TW 5690 | E. faecium | vanB | +++ | +++ | ++ | + | 50 | 10 | 0 |
| 53 | TW 6169 | E. faecalis | vanB | +++ | ++ | + | 40 | 19 | 22 | 8 |
| 54 | TW 6170 | E. faecium | vanB | +++ | +++ | ++ | + | 24 | 2 | 1 |
| 55 | TW 6171 | E. faecium | vanB | +++ | +++ | ++ | + | 60 | 8 | 1 |
| 56 | TW 6172 | E. faecium | vanB | +++ | +++ | ++ | + | 40 | 3 | 0 |
| 57 | TW 6173 | E. faecium | vanB | +++ | +++ | ++ | + | 40 | 5 | 3 |
| 58 | TW 6174 | E. faecium | vanB | +++ | +++ | ++ | + | 60 | 11 | 4 |
| 59 | TW 6175 | E. faecium | vanB | +++ | +++ | ++ | + | 25 | 1 | 2 |
| 60 | TW 6176 | E. faecium | vanB | +++ | +++ | ++ | + | 50 | 6 | 2 |
| 61 | TW 6177 | E. faecalis | vanB | +++ | +++ | ++ | + | 20 | 18 | 3 |
| 62 | TW 6178 | E. faecium | vanB | +++ | +++ | ++ | + | 40 | 4 | 0 |
| 63 | TW 6179 | E. faecalis | vanB | +++ | + | 100 | 10 | 1 | 2 | 0 |
| 64 | TW 6180 | E. faecium | vanB | +++ | +++ | ++ | + | 40 | 9 | 1 |
| 65 | TW 6181 | E. faecium | vanB | +++ | +++ | ++ | + | 50 | 8 | 5 |
| 66 | TW 6183 | E. faecalis | vanB | +++ | ++ | + | 40 | 14 | 4 | 0 |
| 67 | TW 6184 | E. faecalis | vanB | +++ | ++ | + | 100 | 13 | 3 | 0 |
| 68 | TW 6185 | E. faecium | vanB | +++ | +++ | ++ | + | 60 | 2 | 0 |
| 69 | TW 7515 | E. faecalis | vanB | +++ | ++ | + | 100 | 30 | 4 | 1 |
| 70 | TW 7516 | E. faecalis | vanB | +++ | ++ | + | 80 | 15 | 5 | 0 |

TABLE 7

Number of colony growth on each medium in a dilution culture test (incubated at 35° C. for 48 hours)

| | | | | | Enterococcosel agar with 8 μg/ml of vancomycin Dilution | | | | | | |
|---|---|---|---|---|---|---|---|---|---|---|---|
| Seq. | Organism # | Strains | Resistance gene | Undiluted solution | $\times 10^{-1}$ | $\times 10^{-2}$ | $\times 10^{-3}$ | $\times 10^{-4}$ | $\times 10^{-5}$ | $\times 10^{-6}$ |
| 1 | E. faecalis ATCC 29212 | E. faecalis | None | 0 | 0 | 0 | 0 | 0 | 0 | 0 |
| 2 | E. faecalis Control 1 | E. faecalis | None | 0 | 0 | 0 | 0 | 0 | 0 | 0 |
| 3 | E. faecalis Control 2 | E. faecalis | None | 0 | 0 | 0 | 0 | 0 | 0 | 0 |
| 4 | E. faecalis Control 3 | E. faecalis | None | 0 | 0 | 0 | 0 | 0 | 0 | 0 |
| 5 | E. faecium Control 1 | E. faecium | None | 0 | 0 | 0 | 0 | 0 | 0 | 0 |
| 6 | E. faecium Control 2 | E. faecium | None | 0 | 0 | 0 | 0 | 0 | 0 | 0 |
| 7 | E. faecium Control 3 | E. faecium | None | 0 | 0 | 0 | 0 | 0 | 0 | 0 |
| 8 | E. avium Control 1 | E. avium | None | 0 | 0 | 0 | 0 | 0 | 0 | 0 |
| 9 | E. avium Control 2 | E. avium | None | 0 | 0 | 0 | 0 | 0 | 0 | 0 |
| 10 | E. avium Control 3 | E. avium | None | 0 | 0 | 0 | 0 | 0 | 0 | 0 |
| 11 | E. casseliflavus Control 1 | E. casseliflavus | vanC | +++ | +++ | ++ | + | (41) | 5 | 0 |
| 12 | E. casseliflavus Control 2 | E. casseliflavus | vanC | +++ | +++ | ++ | + | 32 | 3 | 0 |
| 13 | E. casseliflavus Control 3 | E. casseliflavus | vanC | +++ | +++ | ++ | + | 21 | 3 | 0 |
| 14 | E. casseliflavus Control 4 | E. casseliflavus | vanC | +++ | +++ | ++ | + | 26 | 3 | 0 |
| 15 | E. casseliflavus Control 5 | E. casseliflavus | vanC | +++ | +++ | ++ | + | 33 | 1 | 0 |
| 16 | E. gallinarum Control 1 | E. gallinarum | vanC | +++ | +++ | ++ | + | 33 | 4 | 0 |
| 17 | E. gallinarum Control 2 | E. gallinarum | vanC | +++ | +++ | ++ | + | 48 | 4 | 0 |
| 18 | E. gallinarum Control 3 | E. gallinarum | vanC | +++ | +++ | ++ | + | 29 | 6 | 0 |
| 19 | E. gallinarum Control 4 | E. gallinarum | vanC | +++ | +++ | ++ | + | 40 | 2 | 0 |
| 20 | E. gallinarum Control 5 | E. gallinarum | vanC | +++ | +++ | ++ | + | 35 | 1 | 0 |
| 21 | TW 3491 | E. faecium | vanA | +++ | +++ | ++ | + | 55 | 7 | 0 |
| 22 | TW 4558 | E. faecium | vanA | +++ | +++ | ++ | + | 47 | 6 | 0 |
| 23 | TW 4559 | E. faecium | vanA | +++ | +++ | ++ | + | 52 | 6 | 0 |
| 24 | TW 4561 | E. faecium | vanA | +++ | +++ | ++ | + | 48 | 2 | 0 |
| 25 | TW 4590 | E. faecium | vanA | +++ | +++ | ++ | + | 51 | 2 | 0 |
| 26 | TW 3492 | E. faecium | vanB | +++ | +++ | ++ | + | 100 | 12 | 0 |
| 27 | TW 4560 | E. faecium | vanB | + | (+) | 1 | 0 | 0 | 0 | 0 |
| 28 | TW 4589 | E. faecalis | vanB | +++ | ++ | + | 100 | 18 | 2 | 2 |
| 29 | TW 5246 | E. faecalis | vanB | +++ | ++ | + | 100 | 40 | 4 | 1 |
| 30 | TW 5247 | E. faecium | vanB | +++ | +++ | ++ | + | 70 | 7 | 0 |
| 31 | TW 5604 | E. faecium | vanB | +++ | +++ | (+) | (200) | 0 | 0 | 0 |
| 32 | TW 5607 | E. faecium | vanB | +++ | +++ | ++ | + | 100 | 20 | 5 |
| 33 | TW 5608 | E. faecalis | vanB | +++ | ++ | + | 80 | 19 | 12 | 1 |
| 34 | TW 5609 | E. faecalis | vanB | +++ | ++ | + | 70 | 6 | 15 | 0 |
| 35 | TW 5610 | E. faecalis | vanB | +++ | ++ | + | 100 | 50 | 40 | 5 |
| 36 | TW 5611 | E. faecalis | vanB | +++ | ++ | + | 100 | 30 | 20 | 2 |
| 37 | TW 5645 | E. faecalis | vanB | +++ | +++ | ++ | + | 30 | 8 | 1 |
| 38 | TW 5646 | E. faecium | vanB | +++ | +++ | ++ | + | 40 | 25 | 1 |
| 39 | TW 5668 | E. faecalis | vanB | +++ | +++ | ++ | + | 50 | 7 | 0 |
| 40 | TW 5669 | E. faecium | vanB | +++ | +++ | ++ | + | 100 | 4 | 1 |
| 41 | TW 5670 | E. faecium | vanB | +++ | +++ | ++ | + | 60 | 10 | 1 |
| 42 | TW 5671 | E. faecium | vanB | +++ | ++ | + | 12 | 1 | 0 | 0 |
| 43 | TW 5672 | E. faecium | vanB | +++ | +++ | ++ | + | 17 | 2 | 0 |
| 44 | TW 5682 | E. faecalis | vanB | +++ | +++ | ++ | + | 40 | 1 | 1 |
| 45 | TW 5683 | E. faecalis | vanB | +++ | +++ | ++ | + | 30 | 3 | 2 |
| 46 | TW 5684 | E. faecalis | vanB | +++ | +++ | ++ | + | 25 | 6 | 0 |
| 47 | TW 5685 | E. faecalis | vanB | +++ | ++ | + | 40 | 2 | 0 | 0 |
| 48 | TW 5686 | E. faecalis | vanB | +++ | ++ | + | 20 | 1 | 0 | 0 |
| 49 | TW 5687 | E. faecalis | vanB | ++ | + | 100 | 4 | 0 | 0 | 0 |
| 50 | TW 5688 | E. faecium | vanB | +++ | ++ | + | (+) | (30) | 0 | 0 |
| 51 | TW 5689 | E. faecium | vanB | +++ | +++ | ++ | + | 30 | 1 | 1 |
| 52 | TW 5690 | E. faecium | vanB | +++ | +++ | ++ | + | 50 | 6 | 1 |
| 53 | TW 6169 | E. faecalis | vanB | +++ | ++ | + | 30 | 15 | 13 | 1 |
| 54 | TW 6170 | E. faecalis | vanB | +++ | ++ | + | 60 | 14 | 1 | 0 |
| 55 | TW 6171 | E. faecium | vanB | +++ | +++ | ++ | + | 30 | 17 | 2 |
| 56 | TW 6172 | E. faecium | vanB | +++ | ++ | + | (100) | (20) | (5) | 0 |
| 57 | TW 6173 | E. faecium | vanB | +++ | +++ | ++ | + | 46 | 6 | 2 |
| 58 | TW 6174 | E. faecium | vanB | +++ | (+) | (40) | 0 | 0 | 0 | 0 |
| 59 | TW 6175 | E. faecium | vanB | +++ | ++ | + | + | 21 | 6 | 0 |
| 60 | TW 6176 | E. faecium | vanB | +++ | +++ | ++ | + | 50 | 7 | 0 |
| 61 | TW 6177 | E. faecalis | vanB | +++ | +++ | ++ | + | 30 | 20 | 6 |
| 62 | TW 6178 | E. faecium | vanB | +++ | +++ | ++ | + | 30 | 4 | 0 |
| 63 | TW 6179 | E. faecalis | vanB | ++ | + | 50 | 5 | 1 | 0 | 0 |
| 64 | TW 6180 | E. faecium | vanB | +++ | (++) | (+) | 1 | 0 | 0 | 0 |
| 65 | TW 6181 | E. faecium | vanB | +++ | +++ | ++ | + | 50 | 11 | 2 |
| 66 | TW 6183 | E. faecalis | vanB | +++ | ++ | + | 40 | 4 | 1 | 0 |
| 67 | TW 6184 | E. faecalis | vanB | +++ | ++ | + | 100 | 18 | 1 | 0 |
| 68 | TW 6185 | E. faecium | vanB | +++ | +++ | ++ | + | 40 | 4 | 2 |
| 69 | TW 7515 | E. faecalis | vanB | +++ | ++ | + | 100 | 20 | 1 | 0 |
| 70 | TW 7516 | E. faecalis | vanB | ++ | + | 40 | 4 | 1 | 0 | 0 |

TABLE 8

Number of colony growth on each medium in a dilution culture test (incubated at 35° C. for 48 hours)

BHI agar with 32 µg/ml of vancomycin, 32 µg/ml of D-cycloserine, 0.2 mol/l of DL-sodium lactate, 20 µg/ml of polymyxin B, 20 µg/ml of aztreonam, 2 µg/ml of amphotericin B, 50 µg/ml of TTC

| Seq. | Organism # | Strains | Resistance gene | Undiluted solution | ×10$^{-1}$ | ×10$^{-2}$ | ×10$^{-3}$ | ×10$^{-4}$ | ×10$^{-5}$ | ×10$^{-6}$ |
|---|---|---|---|---|---|---|---|---|---|---|
| 1 | E. faecalis ATCC 29212 | E. faecalis | None | 0 | 0 | 0 | 0 | 0 | 0 | 0 |
| 2 | E. faecalis Control 1 | E. faecalis | None | 0 | 0 | 0 | 0 | 0 | 0 | 0 |
| 3 | E. faecalis Control 2 | E. faecalis | None | 0 | 0 | 0 | 0 | 0 | 0 | 0 |
| 4 | E. faecalis Control 3 | E. faecalis | None | 0 | 0 | 0 | 0 | 0 | 0 | 0 |
| 5 | E. faecium Control 1 | E. faecium | None | 0 | 0 | 0 | 0 | 0 | 0 | 0 |
| 6 | E. faecium Control 2 | E. faecium | None | 0 | 0 | 0 | 0 | 0 | 0 | 0 |
| 7 | E. faecium Control 3 | E. faecium | None | 0 | 0 | 0 | 0 | 0 | 0 | 0 |
| 8 | E. avium Control 1 | E. avium | None | 0 | 0 | 0 | 0 | 0 | 0 | 0 |
| 9 | E. avium Control 2 | E. avium | None | 0 | 0 | 0 | 0 | 0 | 0 | 0 |
| 10 | E. avium Control 3 | E. avium | None | 0 | 0 | 0 | 0 | 0 | 0 | 0 |
| 11 | E. casseliflavus Control 1 | E. casseliflavus | vanC | 0 | 0 | 0 | 0 | 0 | 0 | 0 |
| 12 | E. casseliflavus Control 2 | E. casseliflavus | vanC | 0 | 0 | 0 | 0 | 0 | 0 | 0 |
| 13 | E. casseliflavus Control 3 | E. casseliflavus | vanC | 0 | 0 | 0 | 0 | 0 | 0 | 0 |
| 14 | E. casseliflavus Control 4 | E. casseliflavus | vanC | 0 | 0 | 0 | 0 | 0 | 0 | 0 |
| 15 | E. casseliflavus Control 5 | E. casseliflavus | vanC | 0 | 0 | 0 | 0 | 0 | 0 | 0 |
| 16 | E. gallinarum Control 1 | E. gallinarum | vanC | 0 | 0 | 0 | 0 | 0 | 0 | 0 |
| 17 | E. gallinarum Control 2 | E. gallinarum | vanC | 0 | 0 | 0 | 0 | 0 | 0 | 0 |
| 18 | E. gallinarum Control 3 | E. gallinarum | vanC | 0 | 0 | 0 | 0 | 0 | 0 | 0 |
| 19 | E. gallinarum Control 4 | E. gallinarum | vanC | 0 | 0 | 0 | 0 | 0 | 0 | 0 |
| 20 | E. gallinarum Control 5 | E. gallinarum | vanC | 0 | 0 | 0 | 0 | 0 | 0 | 0 |
| 21 | TW 3491 | E. faecium | vanA | +++ | +++ | ++ | + | 62 | 11 | 0 |
| 22 | TW 4558 | E. faecium | vanA | +++ | +++ | ++ | + | 43 | 2 | 0 |
| 23 | TW 4559 | E. faecium | vanA | +++ | +++ | ++ | + | 42 | 2 | 0 |
| 24 | TW 4561 | E. faecium | vanA | +++ | +++ | ++ | + | 60 | 3 | 0 |
| 25 | TW 4590 | E. faecium | vanA | +++ | +++ | ++ | + | 59 | 6 | 0 |
| 26 | TW 3492 | E. faecium | vanB | +++ | +++ | ++ | + | 100 | 13 | 2 |
| 27 | TW 4560 | E. faecium | vanB | +++ | +++ | ++ | + | 50 | 4 | 2 |
| 28 | TW 4589 | E. faecalis | vanB | +++ | ++ | + | 100 | 30 | 10 | 0 |
| 29 | TW 5246 | E. faecalis | vanB | +++ | ++ | + | 100 | 30 | 2 | 0 |
| 30 | TW 5247 | E. faecium | vanB | +++ | +++ | ++ | + | 60 | 7 | 1 |
| 31 | TW 5604 | E. faecium | vanB | +++ | +++ | ++ | + | 80 | 8 | 3 |
| 32 | TW 5607 | E. faecium | vanB | +++ | +++ | ++ | + | 100 | 12 | 1 |
| 33 | TW 5608 | E. faecalis | vanB | +++ | ++ | + | 60 | 25 | 13 | 2 |
| 34 | TW 5609 | E. faecalis | vanB | +++ | ++ | + | 70 | 10 | 1 | 0 |
| 35 | TW 5610 | E. faecalis | vanB | +++ | ++ | + | 100 | 50 | 50 | 8 |
| 36 | TW 5611 | E. faecalis | vanB | +++ | ++ | + | 100 | 70 | 60 | 10 |
| 37 | TW 5645 | E. faecium | vanB | +++ | +++ | ++ | + | 30 | 3 | 1 |
| 38 | TW 5646 | E. faecium | vanB | +++ | +++ | ++ | + | 40 | 25 | 3 |
| 39 | TW 5668 | E. faecium | vanB | +++ | +++ | ++ | + | 50 | 5 | 1 |
| 40 | TW 5669 | E. faecium | vanB | +++ | +++ | ++ | + | 100 | 6 | 2 |
| 41 | TW 5670 | E. faecium | vanB | +++ | +++ | ++ | + | 80 | 2 | 1 |
| 42 | TW 5671 | E. faecium | vanB | +++ | +++ | ++ | + | 50 | 5 | 0 |
| 43 | TW 5672 | E. faecium | vanB | +++ | +++ | ++ | + | 30 | 0 | 0 |
| 44 | TW 5682 | E. faecalis | vanB | +++ | +++ | ++ | + | 60 | 6 | 0 |
| 45 | TW 5683 | E. faecalis | vanB | +++ | +++ | ++ | + | 40 | 1 | 0 |
| 46 | TW 5684 | E. faecalis | vanB | +++ | +++ | ++ | + | 20 | 7 | 0 |
| 47 | TW 5685 | E. faecalis | vanB | +++ | ++ | + | 40 | 1 | 0 | 0 |
| 48 | TW 5686 | E. faecalis | vanB | +++ | ++ | + | 40 | 3 | 0 | 1 |
| 49 | TW 5687 | E. faecalis | vanB | ++ | + | 50 | 7 | 0 | 0 | 0 |
| 50 | TW 5688 | E. faecium | vanB | +++ | +++ | ++ | + | 40 | 3 | 4 |
| 51 | TW 5689 | E. faecium | vanB | +++ | +++ | ++ | + | 40 | 4 | 0 |
| 52 | TW 5690 | E. faecium | vanB | +++ | +++ | ++ | + | 40 | 9 | 0 |
| 53 | TW 6169 | E. faecalis | vanB | +++ | ++ | + | 40 | 28 | 15 | 4 |
| 54 | TW 6170 | E. faecalis | vanB | +++ | ++ | + | 100 | 30 | 2 | 0 |
| 55 | TW 6171 | E. faecium | vanB | +++ | ++ | + | 100 | 30 | 5 | 0 |
| 56 | TW 6172 | E. faecium | vanB | +++ | +++ | ++ | + | 30 | 7 | 2 |
| 57 | TW 6173 | E. faecium | vanB | +++ | +++ | ++ | + | 40 | 7 | 2 |
| 58 | TW 6174 | E. faecium | vanB | +++ | +++ | ++ | + | 50 | 5 | 2 |
| 59 | TW 6175 | E. faecium | vanB | +++ | +++ | ++ | + | 20 | 1 | 1 |
| 60 | TW 6176 | E. faecium | vanB | +++ | +++ | ++ | + | 50 | 15 | 2 |
| 61 | TW 6177 | E. faecalis | vanB | +++ | +++ | ++ | + | 20 | 11 | 2 |
| 62 | TW 6178 | E. faecium | vanB | +++ | +++ | ++ | + | 30 | 7 | 0 |
| 63 | TW 6179 | E. faecalis | vanB | ++ | + | 50 | 6 | 1 | 0 | 0 |
| 64 | TW 6180 | E. faecium | vanB | +++ | +++ | ++ | + | 40 | 8 | 3 |
| 65 | TW 6181 | E. faecium | vanB | +++ | +++ | ++ | + | 50 | 8 | 5 |
| 66 | TW 6183 | E. faecalis | vanB | +++ | ++ | + | 40 | 9 | 1 | 1 |
| 67 | TW 6184 | E. faecalis | vanB | +++ | ++ | + | 100 | 13 | 1 | 1 |
| 68 | TW 6185 | E. faecium | vanB | +++ | +++ | ++ | + | 40 | 4 | 0 |

TABLE 8-continued

Number of colony growth on each medium in a dilution culture test (incubated at 35° C. for 48 hours)

| | | | | | BHI agar with 32 µg/ml of vancomycin, 32 µg/ml of D-cycloserine, 0.2 mol/l of DL-sodium lactate, 20 µg/ml of polymyxin B, 20 µg/ml of aztreonam, 2 µg/ml of amphotericin B, 50 µg/ml of TTC Dilution | | | | | | |
|---|---|---|---|---|---|---|---|---|---|---|---|
| Seq. | Organism # | Strains | Resistance gene | Undiluted solution | $\times 10^{-1}$ | $\times 10^{-2}$ | $\times 10^{-3}$ | $\times 10^{-4}$ | $\times 10^{-5}$ | $\times 10^{-6}$ |
| 69 | TW 7515 | E. faecalis | vanB | +++ | ++ | + | 100 | 30 | 2 | 0 |
| 70 | TW 7516 | E. faecalis | vanB | ++ | + | 100 | 15 | 2 | 0 | 0 |

TABLE 9

Strains detected in VRE screening of actual fecal specimens using screening media (incubated at 35° C. for 48 hours)

| | Enterococcosel agar with 8 µg/ml of vancomycin | BHI agar with 32 µg/ml of vancomycin, 32 µg/ml of D-cycloserine, 0.2 mol/l DL-sodium lactete, 20 µg/ml of polymyxin B, 20 µg/ml of aztreonam, 2 µg/ml of amphotericin B and 50 µg/ml TTC |
|---|---|---|
| Number of specimens where van C VRE is detected | 13 pecimens (26.5%) | 0 specimen (0%) |
| Number of specimens where van A and van B VRE are detected | 0 specimen (0%) | 0 specimen (0%) |

TABLE 10

Number of Van B VRE detected in VRE screening of Van B VRE inoculated fecal specimens using screening media (incubated at 35° C. for 48 hours)

| Fecal specimens to which Van B VRE is inoculated | Van B VRE used for inoculation | Amount of inoculum | Enterococcosel agar with 8 µg/ml of vancomycin | BHI agar with 32 µg/ml of vancomycin, 32 µg/ml of D-cycloserine, 0.2 mol/l DL-sodium lactete, 20 µg/ml of polymyxin B, 20 µg/ml of aztreonam, 2 µg/ml of amphotericin B and 50 µg/ml TTC |
|---|---|---|---|---|
| Sample 1 | TW 4560 | 10~20 cells/10 µl | Can not differentiate due to numerous Van C VRE | 16 cells/10 µl |
| | TW 6174 | 10~20 cells/10 µl | Can not differentiate due to numerous Van C VRE | 13 cells/10 µl |
| | TW 6180 | 10~20 cells/10 µl | Can not differentiate due to numerous Van C VRE | 17 cells/10 µl |
| Sample 2 | TW 4560 | 10~20 cells/10 µl | 15 cells/10 µl | 10 cells/10 µl |
| | TW 6174 | 10~20 cells/10 µl | 0 cells/10 µl | 18 cells/10 µl |
| | TW 6180 | 10~20 cells/10 µl | 15 cells/10 µl | 15 cells/10 µl |

The invention claimed is:

1. A Van A and Van B vancomycin resistant *enterococci* detection medium where vancomycin, D-cycloserine and D-lactate are added to a culture medium formula where *enterococci* can grow.

2. A Van A and Van B vancomycin resistant *enterococci* detection medium where 32-256 µg/ml of vancomycin, 1-64 µg/ml of D-cycloserine and 0.025-0.8 mol/l of DL-sodium lactate are added to a culture medium formula where *enterococci* can grow.

3. A method of selectively detecting Van A and Van B vancomycin resistant *enterococci*, comprising inoculating a suspension of a testing microorganism to a Van A and Van B vancomycin resistant *enterococci* detection medium of claim 1, and incubating the medium at 35-37° C. for 24-48 hours.

4. A method of selectively detecting Van A and Van B vancomycin resistant *enterococci*, comprising inoculating a specimen to a Van A and Van B vancomycin resistant *enterococci* detection medium of claim 1, and incubating the medium at 35-37° C. for 24-48 hours.

5. A method of selectively detecting Van A and Van B vancomycin resistant *enterococci*, comprising inoculating suspension of a testing microorganism to a Van A and Van B vancomycin resistant *enterococci* detection medium of claim 2, and incubating the medium at 35-37° C. for 24-48 hours.

6. A method of selectively detecting Van A and Van B vancomycin resistant *enterococci*, comprising inoculating a specimen to a Van A and Van B vancomycin resistant *enterococci* detection medium of claim 2, and incubating the medium at 35-37° C. for 24-48 hours.

7. A method of selectively detecting Van A and Van B vancomycin resistant *enterococci*, comprising inoculating a suspension of a testing microorganism to a Van A and Van B vancomycin resistant detection medium according to claim 1, incubating said medium, and determining whether Van A and Van B vancomycin resistant *enterococci* are present in said detection medium.

8. A method of selectively detecting Van A and Van B vancomycin resistant *enterococci*, comprising inoculating a suspension of a testing microorganism to a Van A and Van B vancomycin resistant detection medium according to claim 2, incubating said medium, and determining whether Van A and Van B vancomycin resistant *enterococci* are present in said detection medium.

* * * * *